United States Patent [19]
Hayakawa et al.

[11] Patent Number: 5,759,156
[45] Date of Patent: Jun. 2, 1998

[54] PERIOD AND FREQUENCY MEASUREMENT DEVICE WITH CORRECTION DEVICE AND METHOD THEREOF

[75] Inventors: Motomu Hayakawa; Tsukasa Kosuda, both of Suwa; Hiroshi Odagiri; Chiaki Nakamura, both of Chiba, all of Japan

[73] Assignees: Seiko Epson Corporation; Seiko Instruments, Inc., both of Tokyo, Japan

[21] Appl. No.: 602,651

[22] Filed: Feb. 16, 1996

[30] Foreign Application Priority Data

| | | | |
|---|---|---|---|
| Feb. 20, 1995 | [JP] | Japan | 7-031019 |
| Oct. 3, 1995 | [JP] | Japan | 7-256619 |
| Feb. 9, 1996 | [JP] | Japan | 8-024511 |

[51] Int. Cl.$^6$ .................................. A61B 5/0205
[52] U.S. Cl. .................................. 600/483; 600/503
[58] Field of Search .................... 128/670, 687, 128/689, 690, 700; 600/483, 500, 502, 503, 513

[56] References Cited

U.S. PATENT DOCUMENTS

| | | |
|---|---|---|
| 4,202,350 | 5/1980 | Walton . |
| 4,224,948 | 9/1980 | Cramer et al. ............ 128/690 |
| 4,407,295 | 10/1983 | Steuer et al. . |
| 5,337,753 | 8/1994 | Lekhtman . |
| 5,511,554 | 4/1996 | Helfenbein et al. ............ 128/670 |
| 5,515,858 | 5/1996 | Myllymaki ............ 128/670 |
| 5,626,140 | 5/1997 | Feldman et al. ............ 128/670 |

FOREIGN PATENT DOCUMENTS

| | | |
|---|---|---|
| 0 614 070 | 9/1994 | European Pat. Off. . |
| 63-34731 | 7/1988 | Japan . |
| 93 14815 | 8/1993 | WIPO . |

*Primary Examiner*—William E. Kamm
*Attorney, Agent, or Firm*—Eric B. Janofsky

[57] ABSTRACT

A period and frequency measurement device is provided having a sensor for measuring pulse waves and body movements. A window determination circuit sets a reference value in accordance with previously measured pulse waves and body movements and determines whether currently measured pulse waves and body movements is within a window defined by upper and lower margins relative to the reference value. A window correction circuit corrects the window to be used for a next pulse waves and body movement measurement by applying a specified correction to the current pulse waves and body movements measurement if a determination result of the window determination circuit indicates that the current pulse waves and body movements measurement is outside a current window.

20 Claims, 18 Drawing Sheets

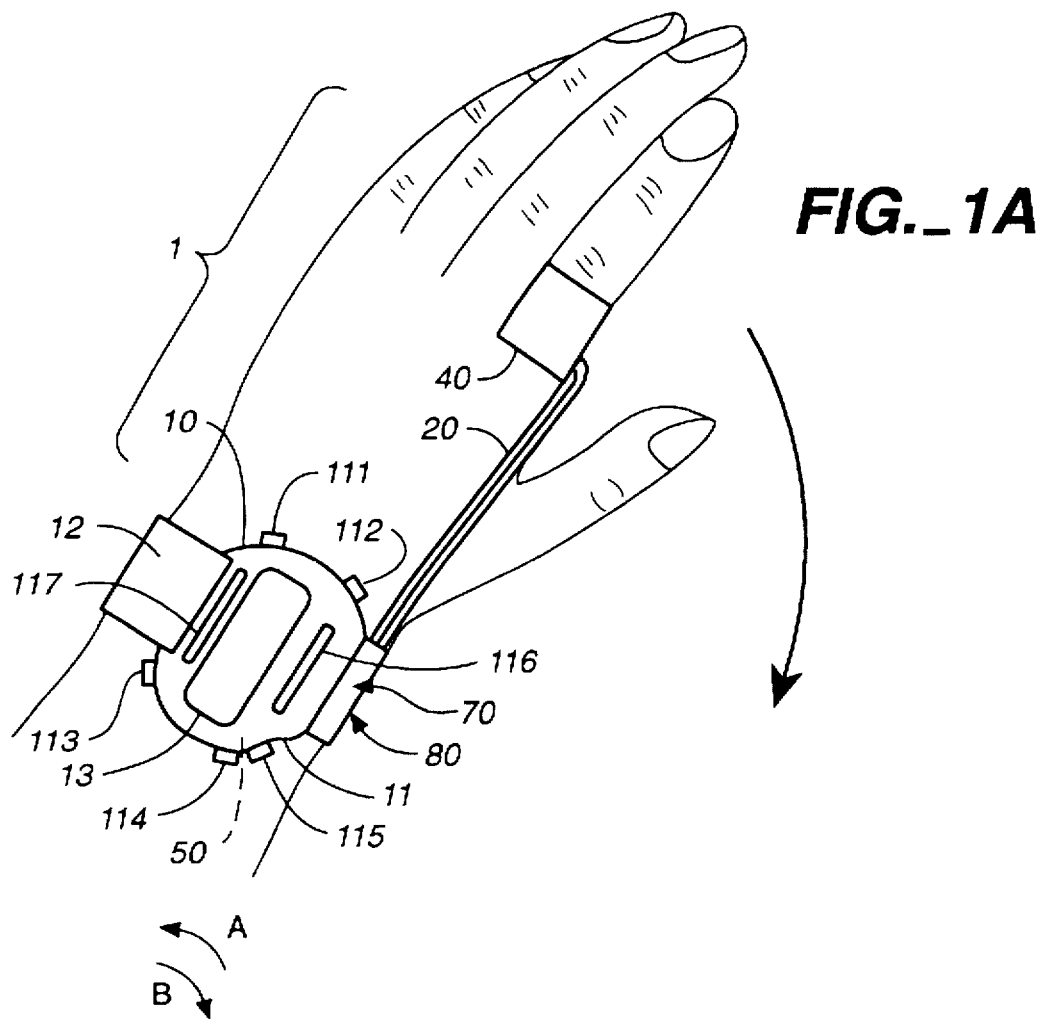
*FIG._1A*
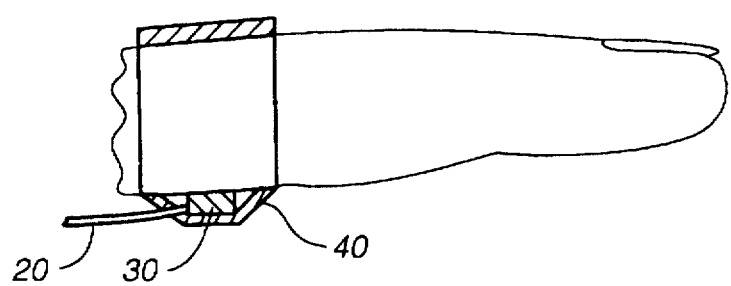
*FIG._1B*

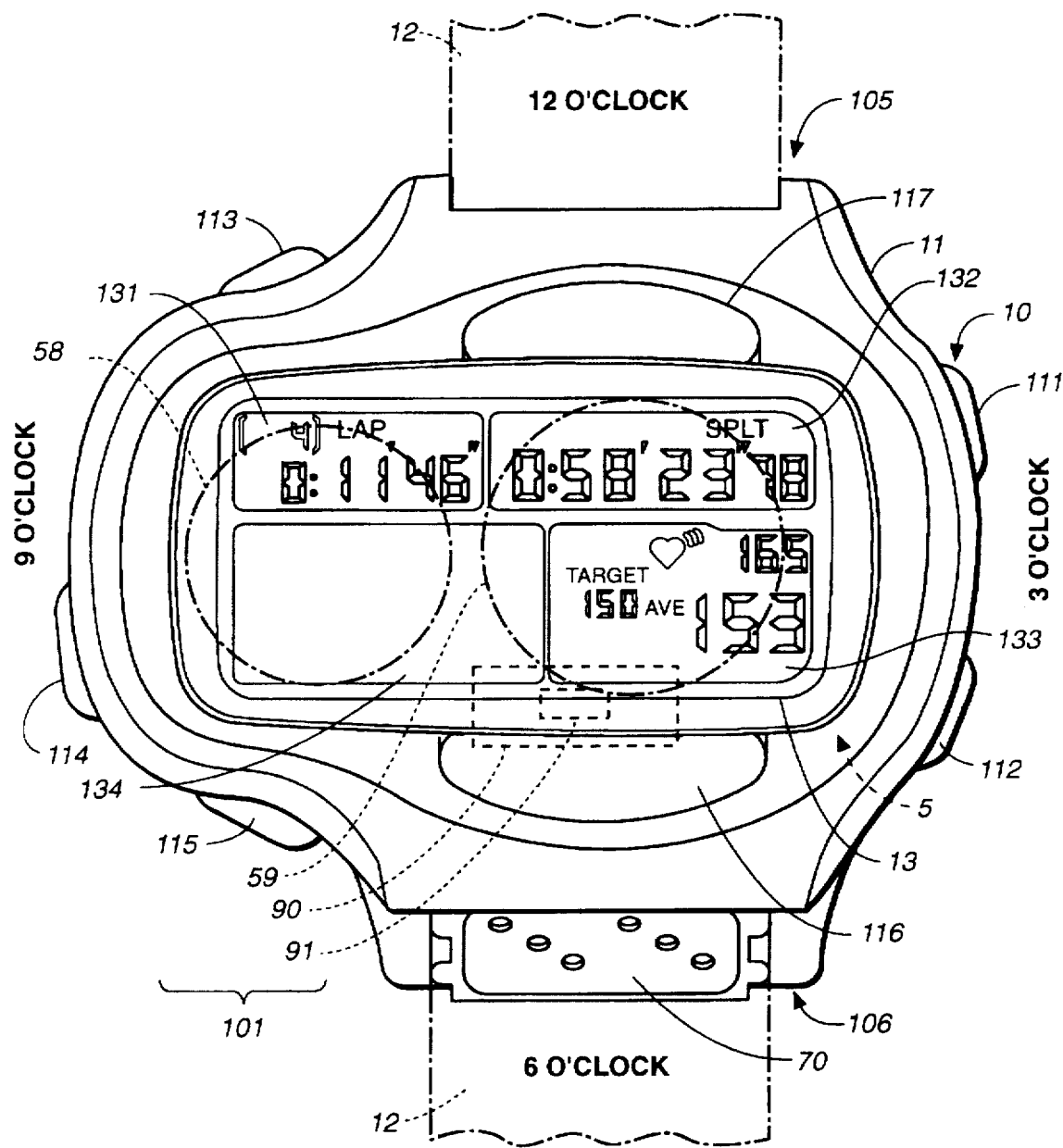
FIG._2

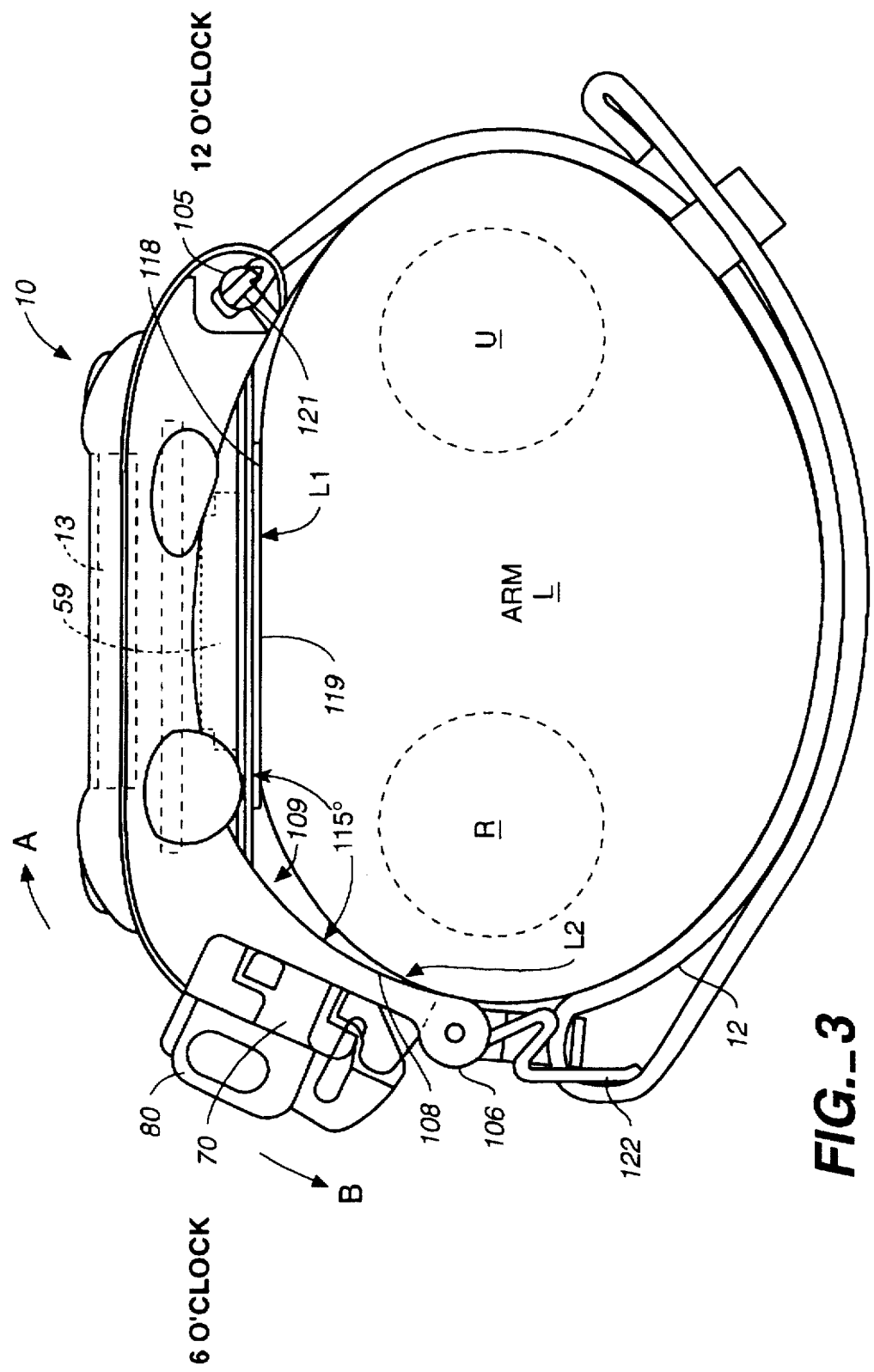
FIG._3

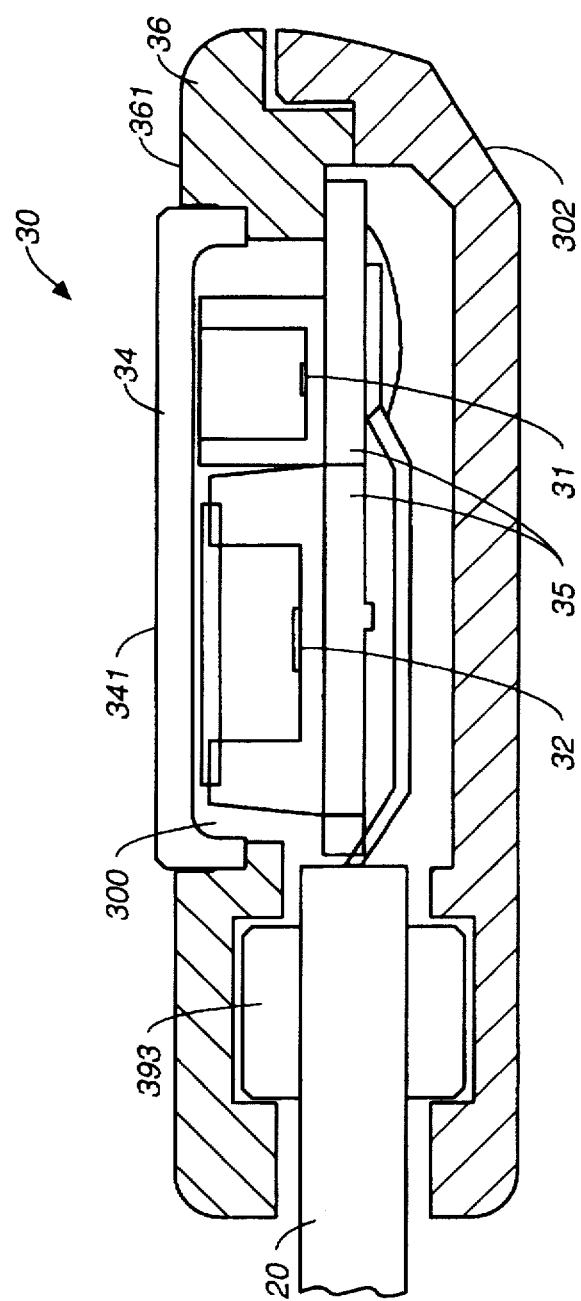
FIG._4

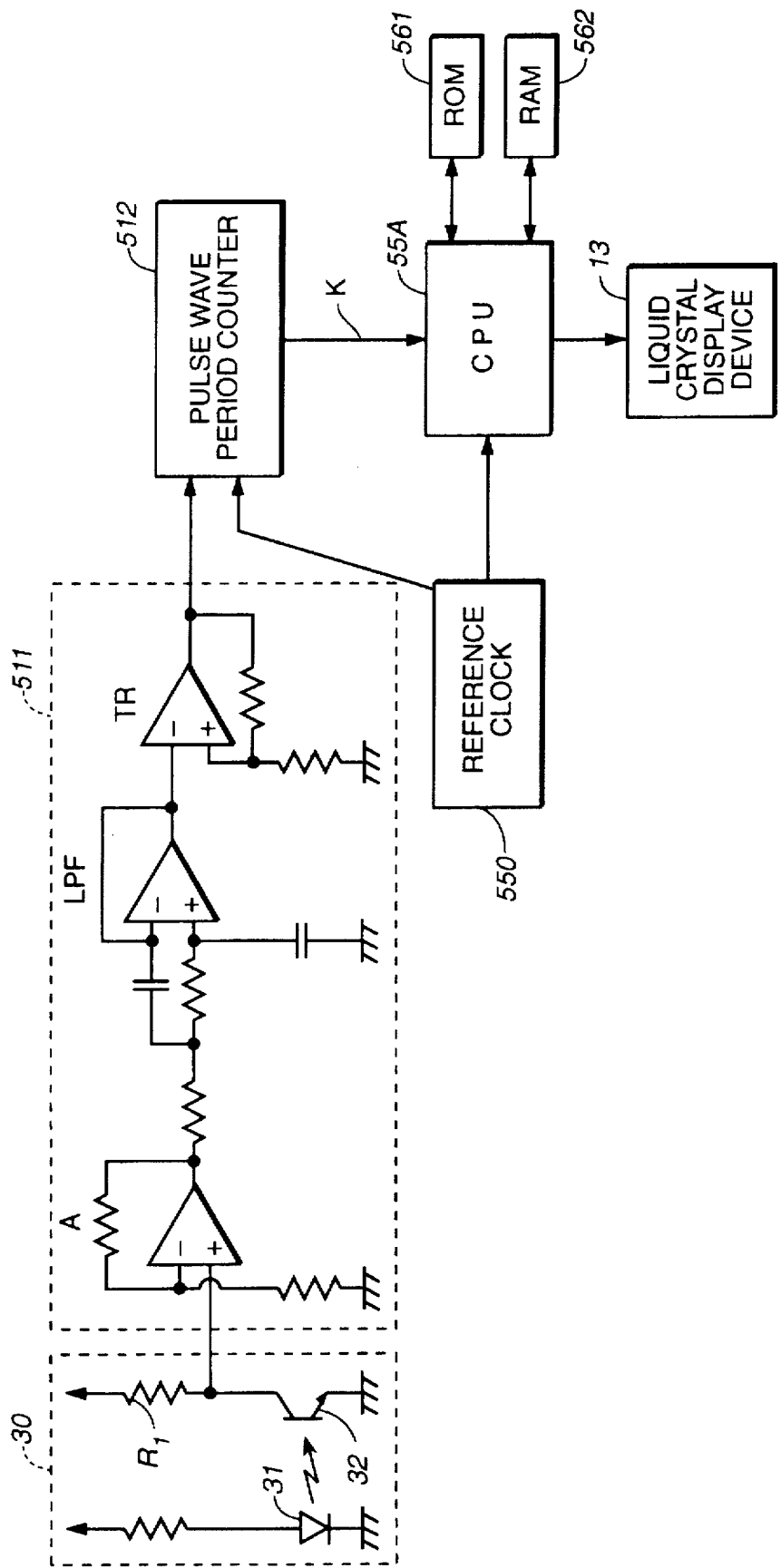
FIG._5

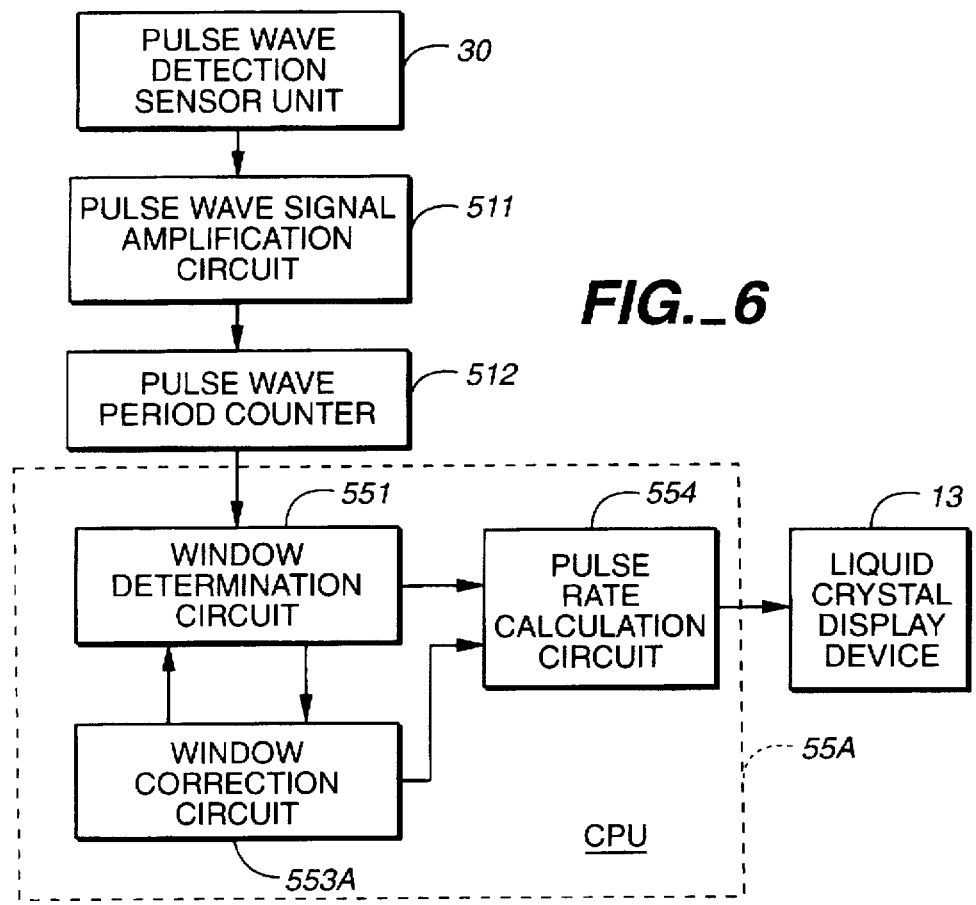
FIG._6
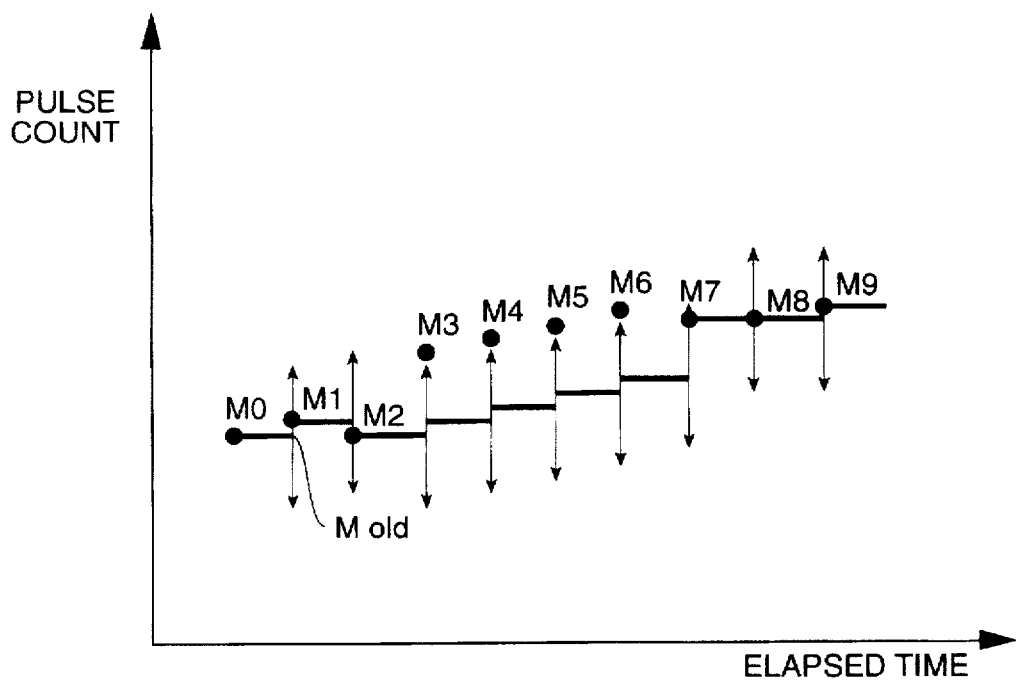
FIG._8

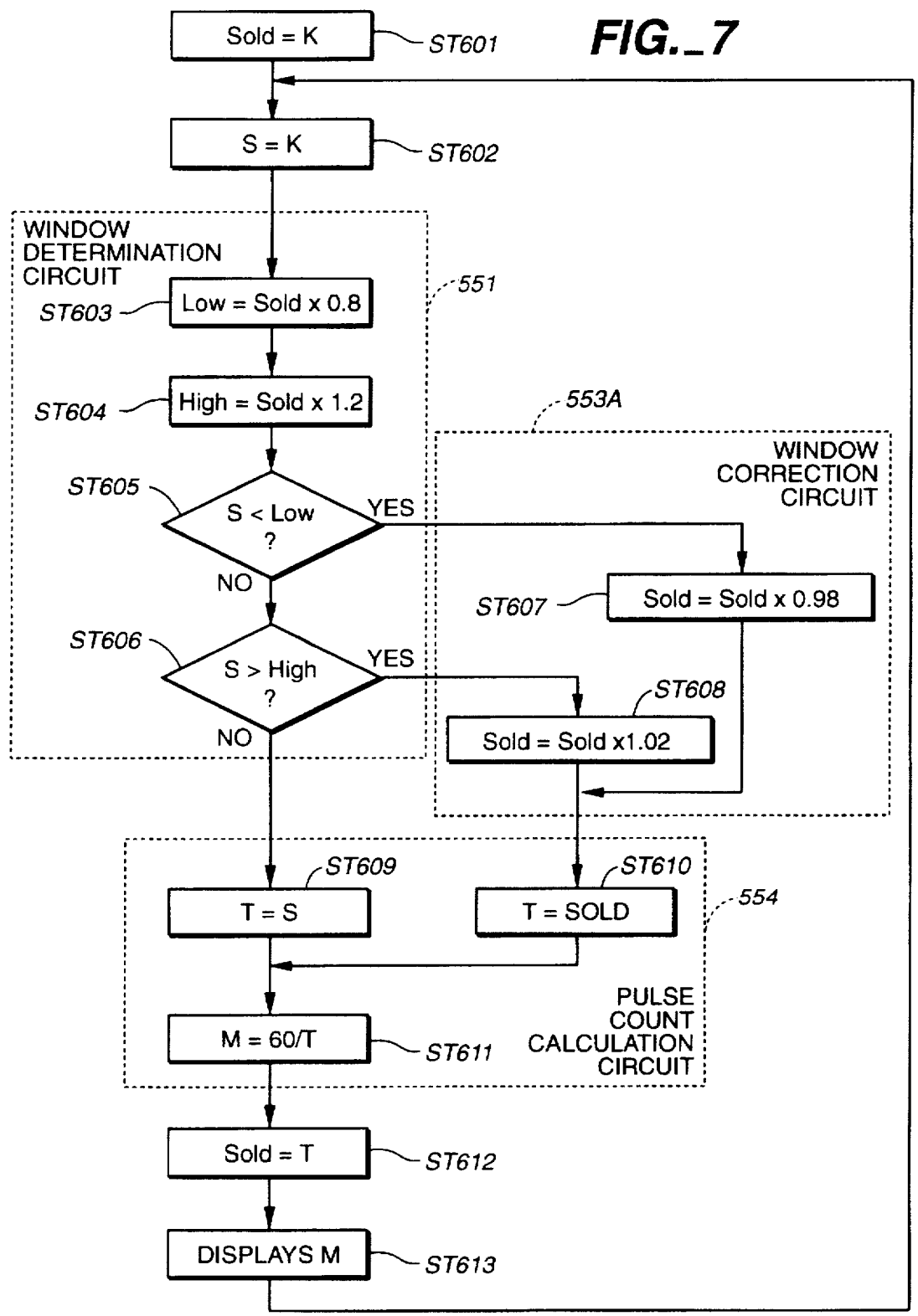
FIG._7

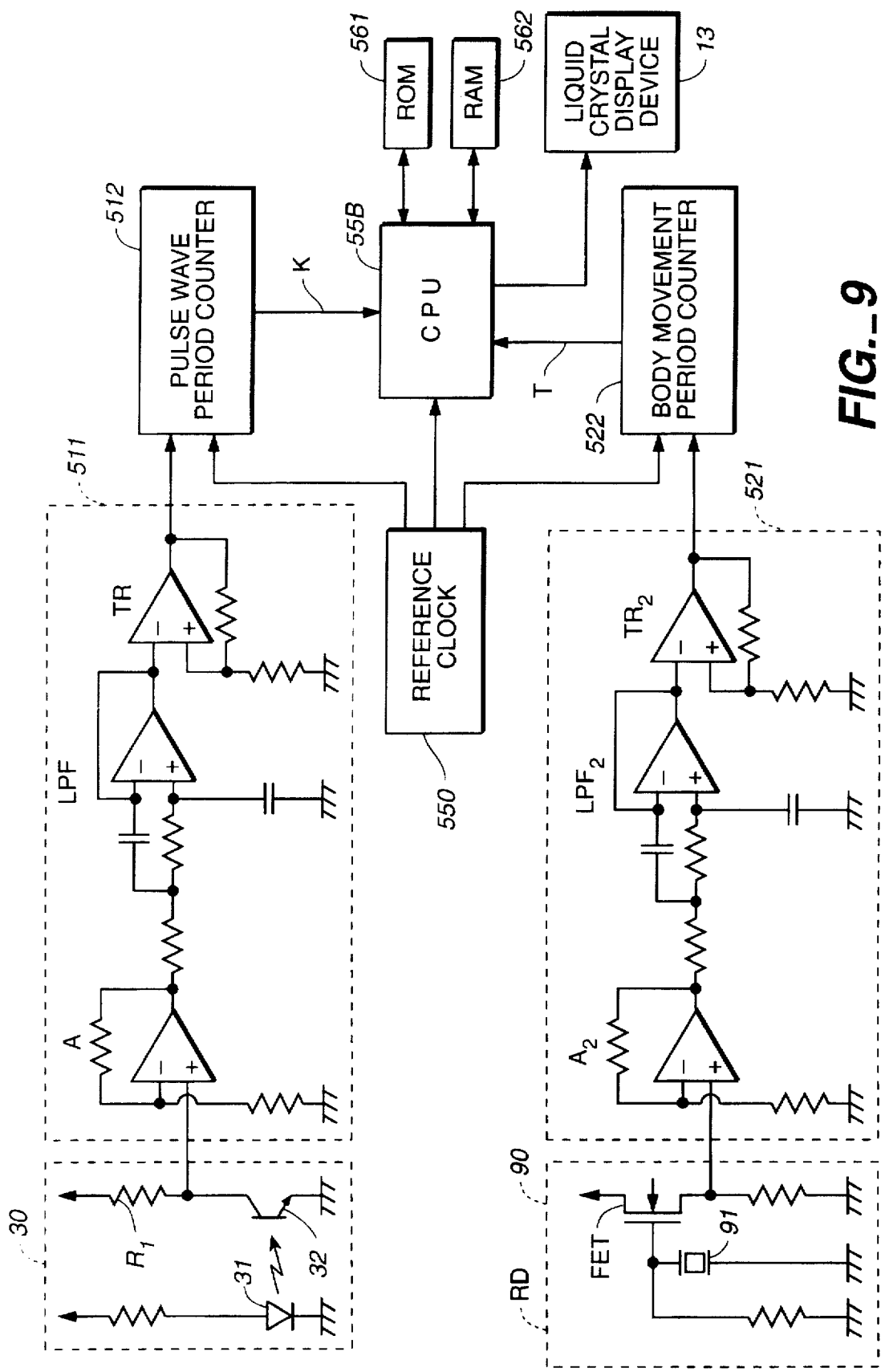
FIG._9

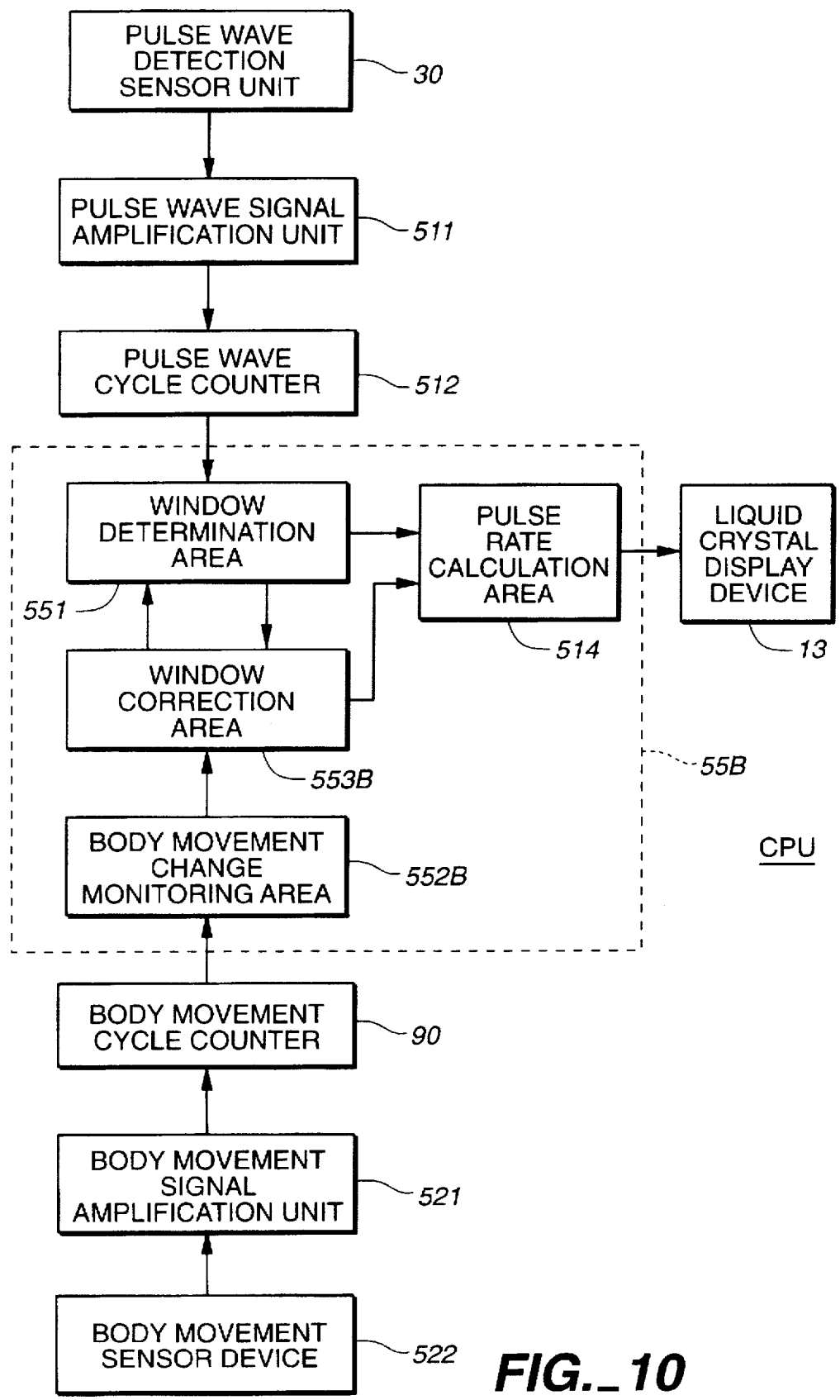
FIG._10

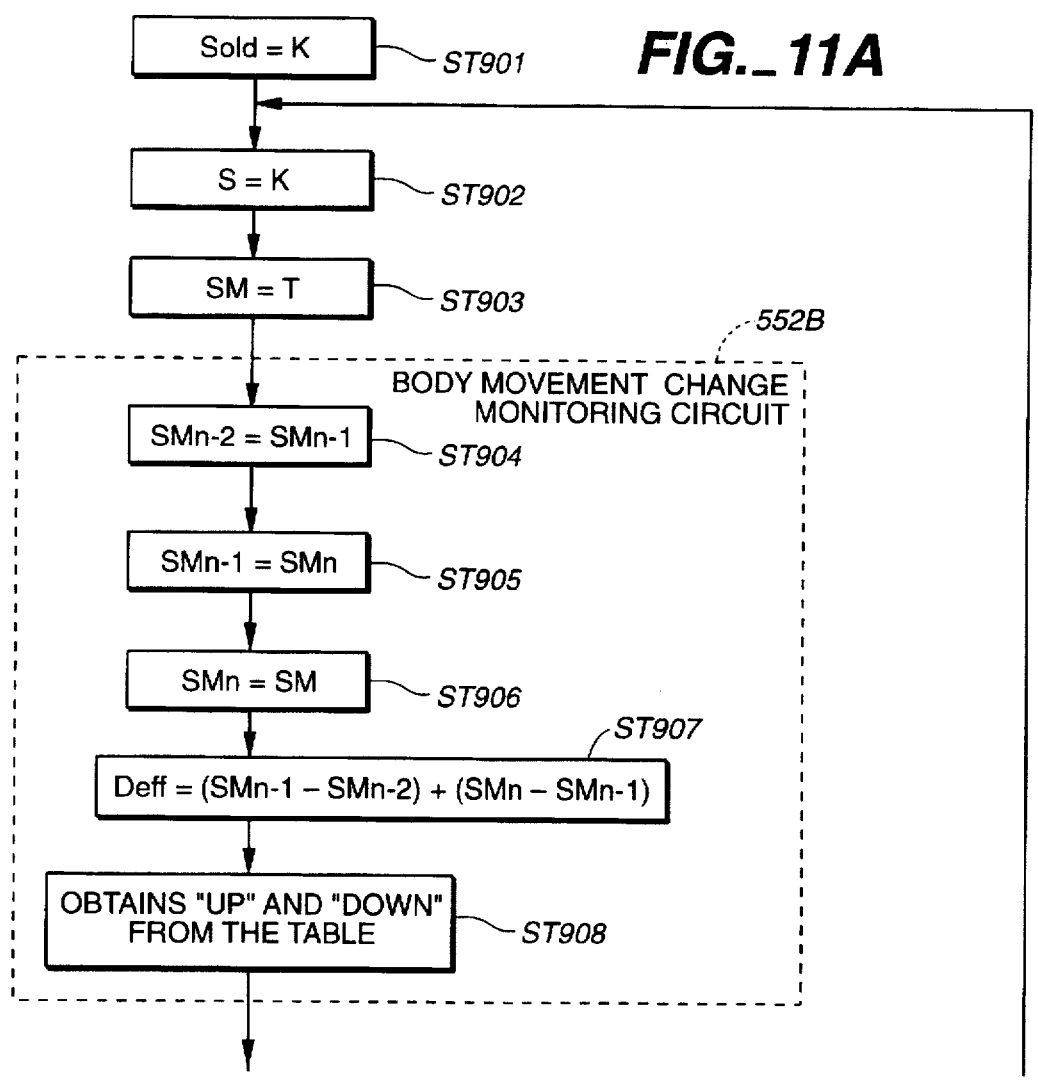

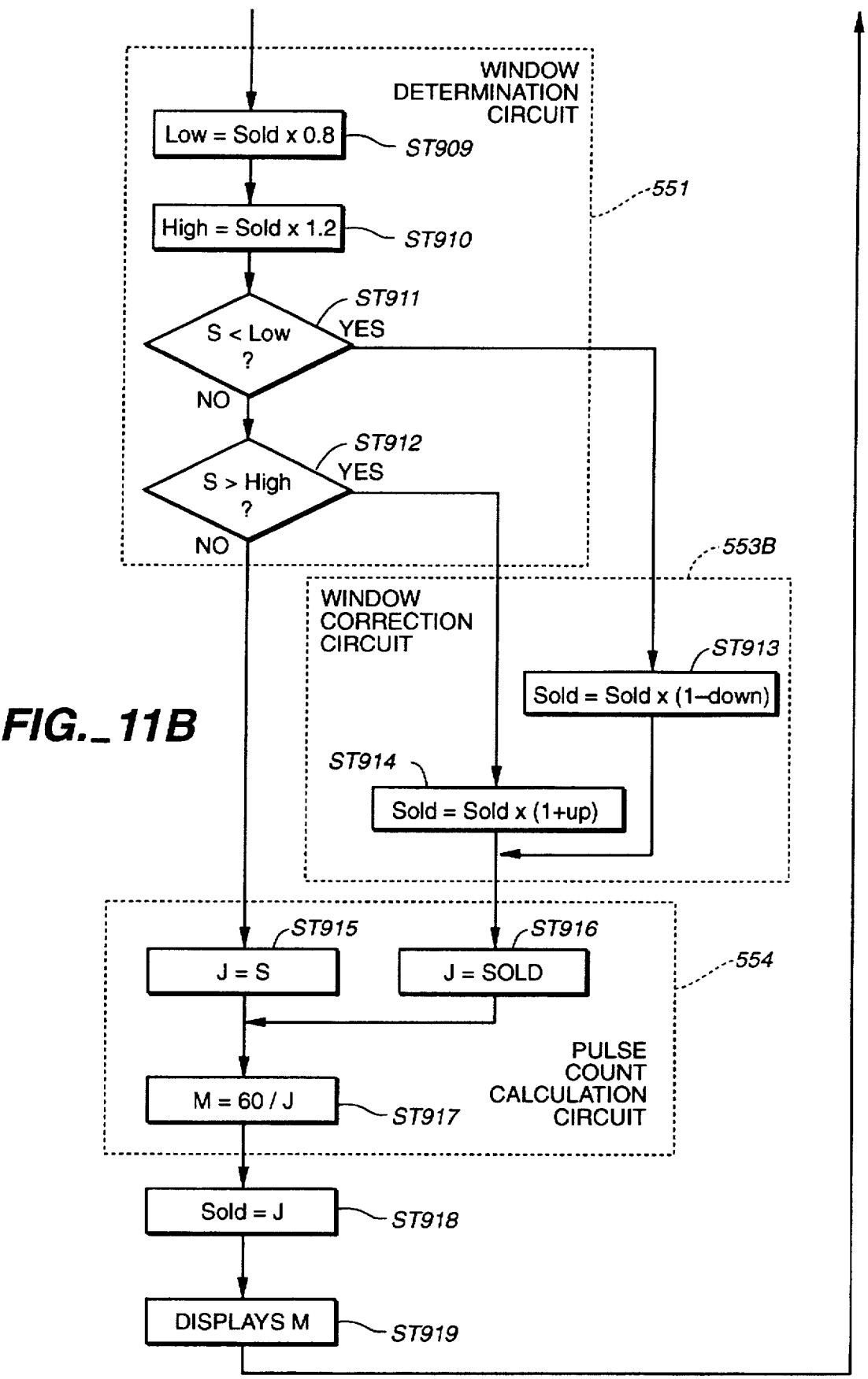
FIG._11B

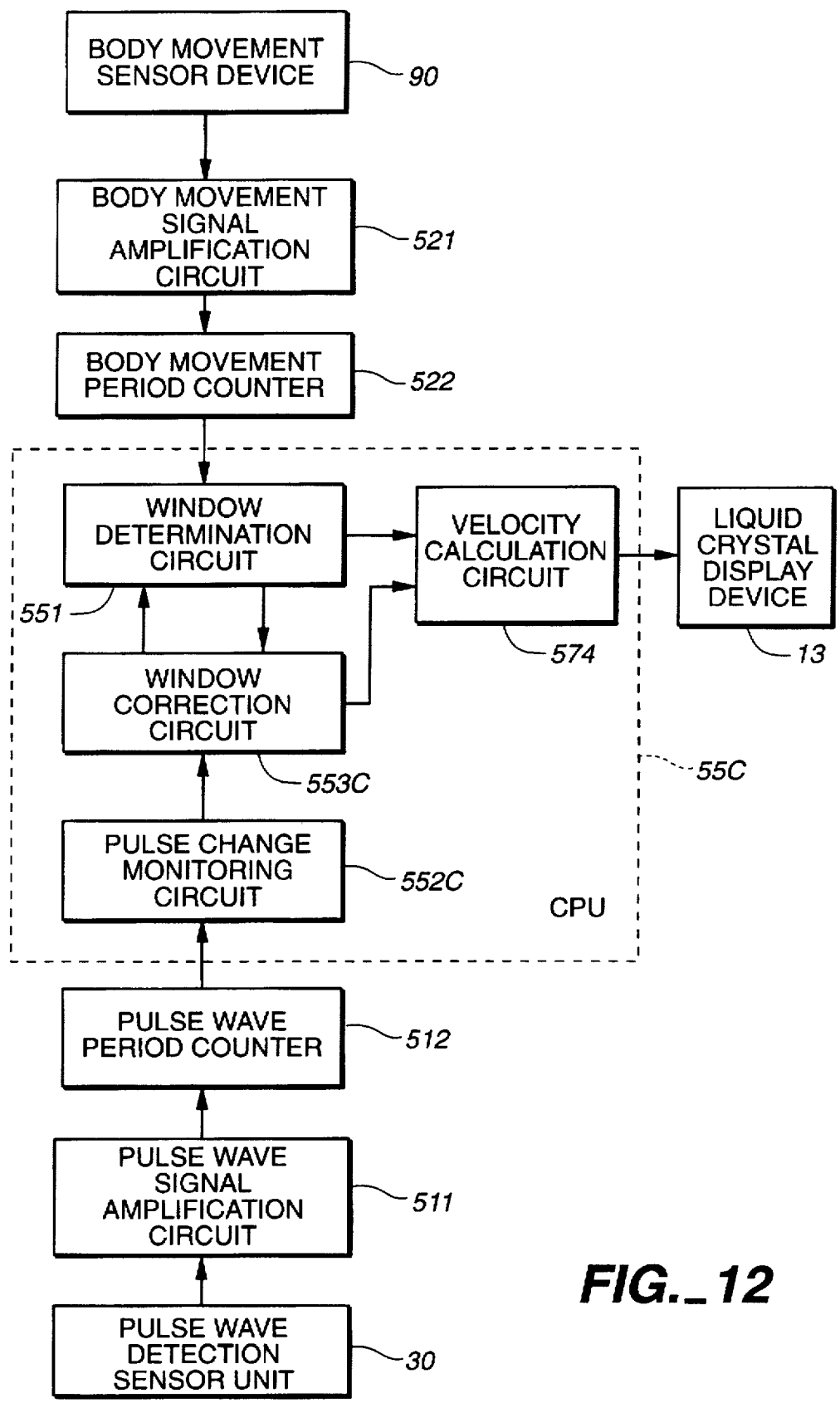
FIG._12

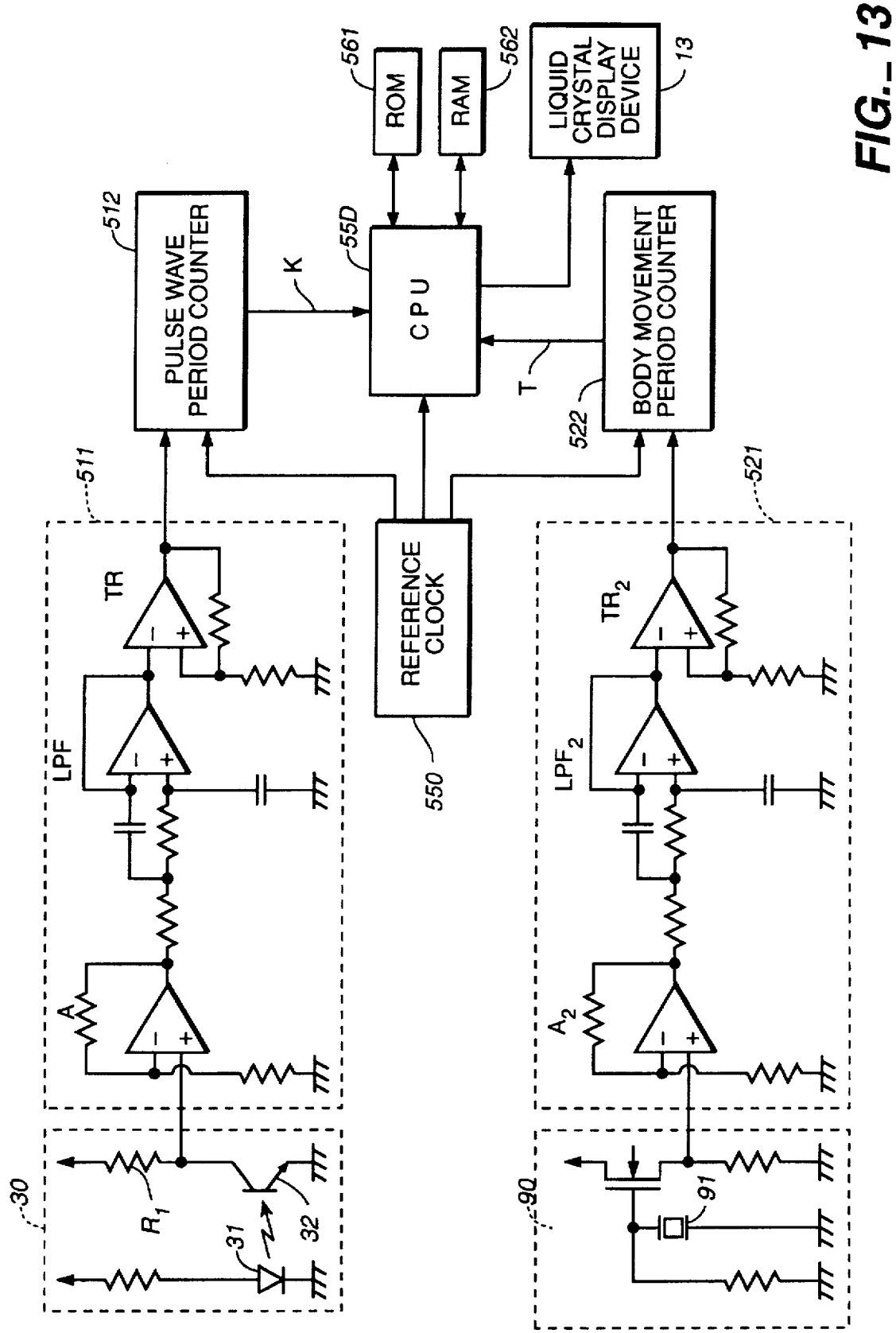
FIG._13

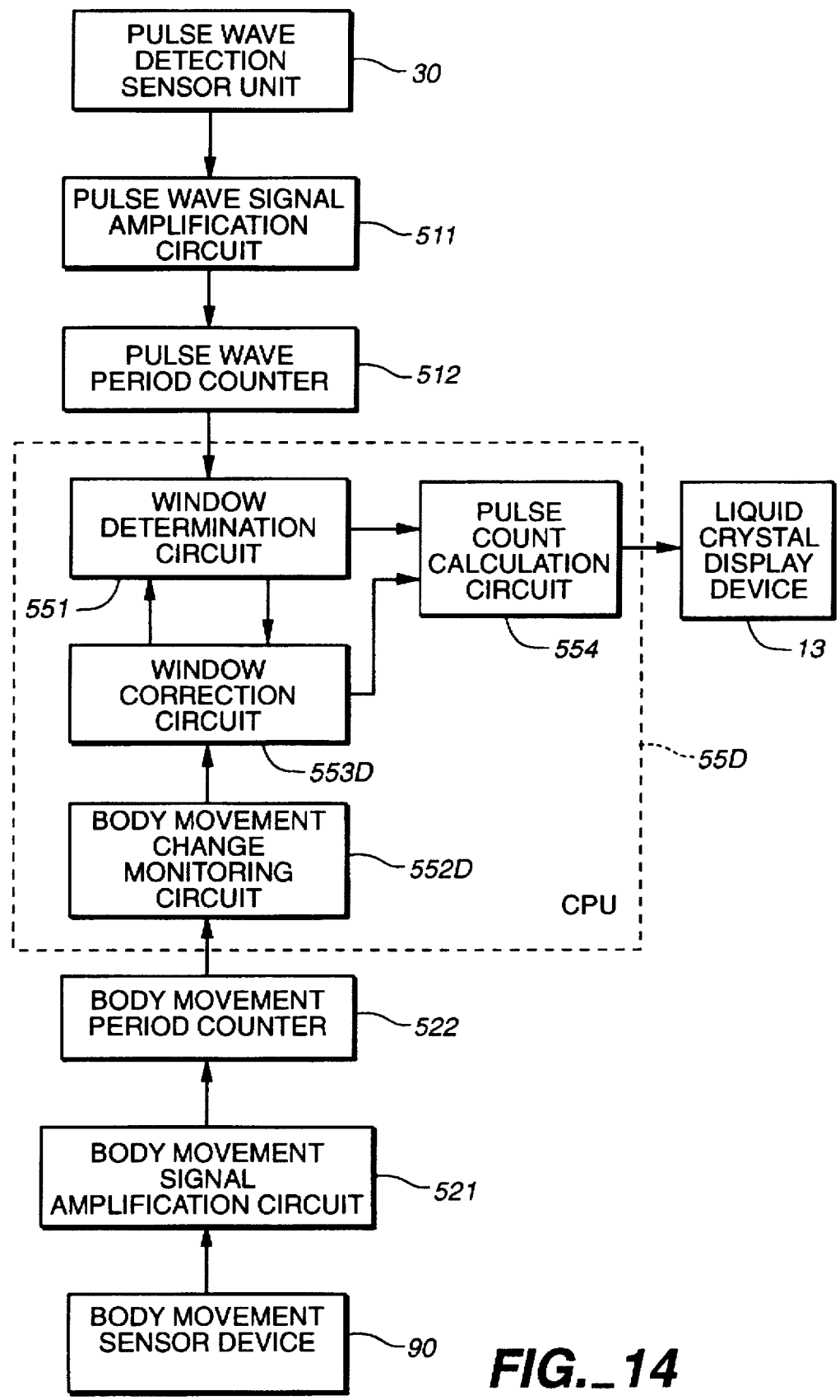
FIG._14

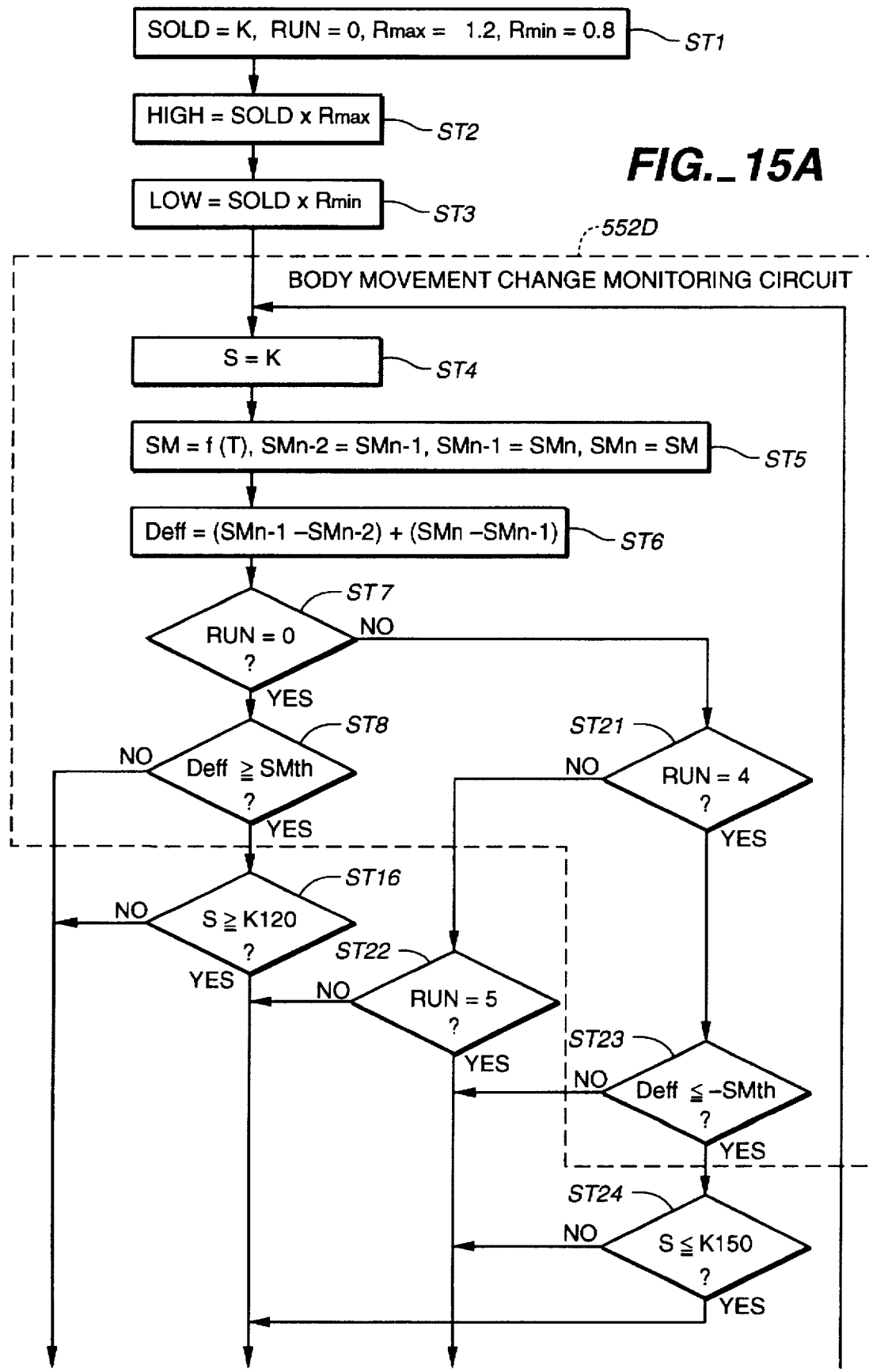
FIG._15A

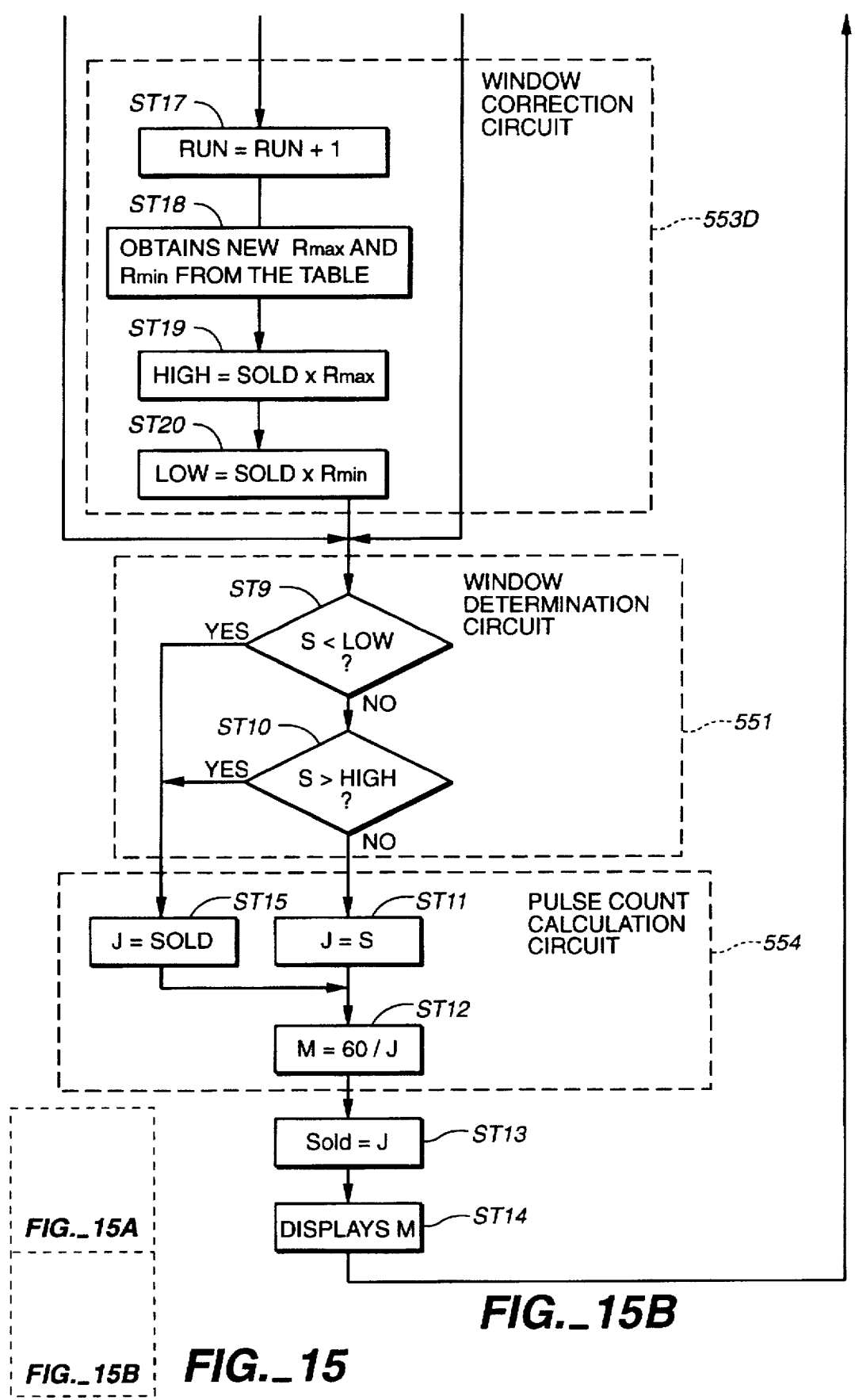

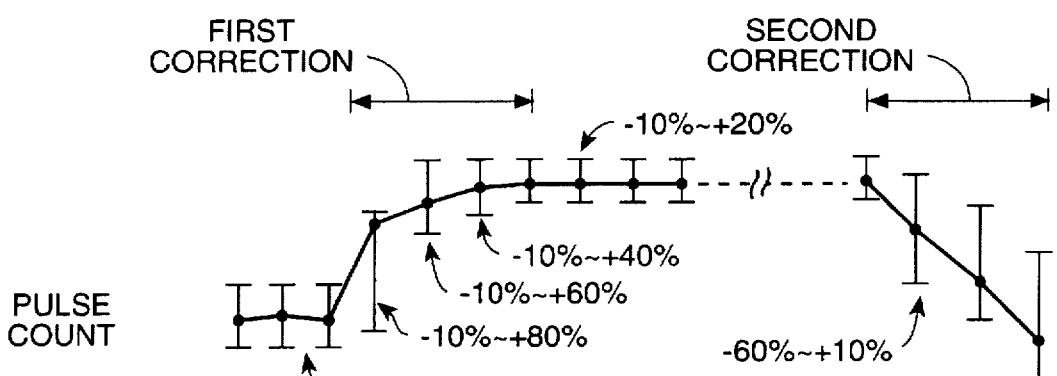
FIG._16A
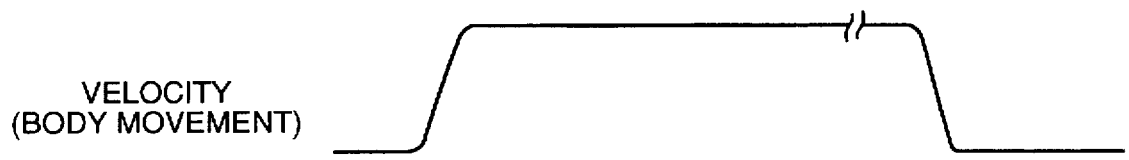
FIG._16B
FIG._16C
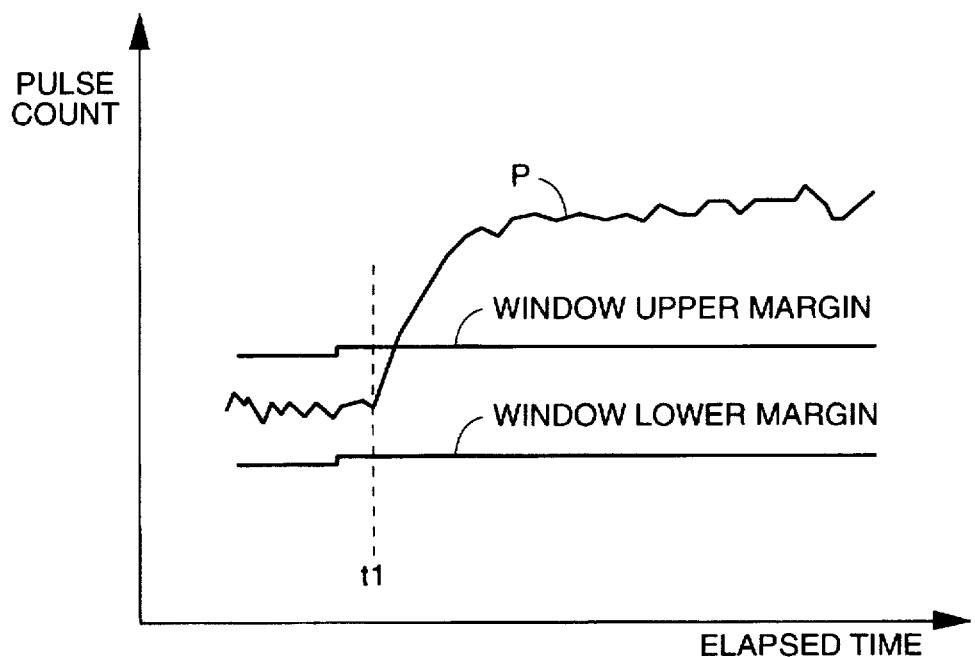
FIG._18

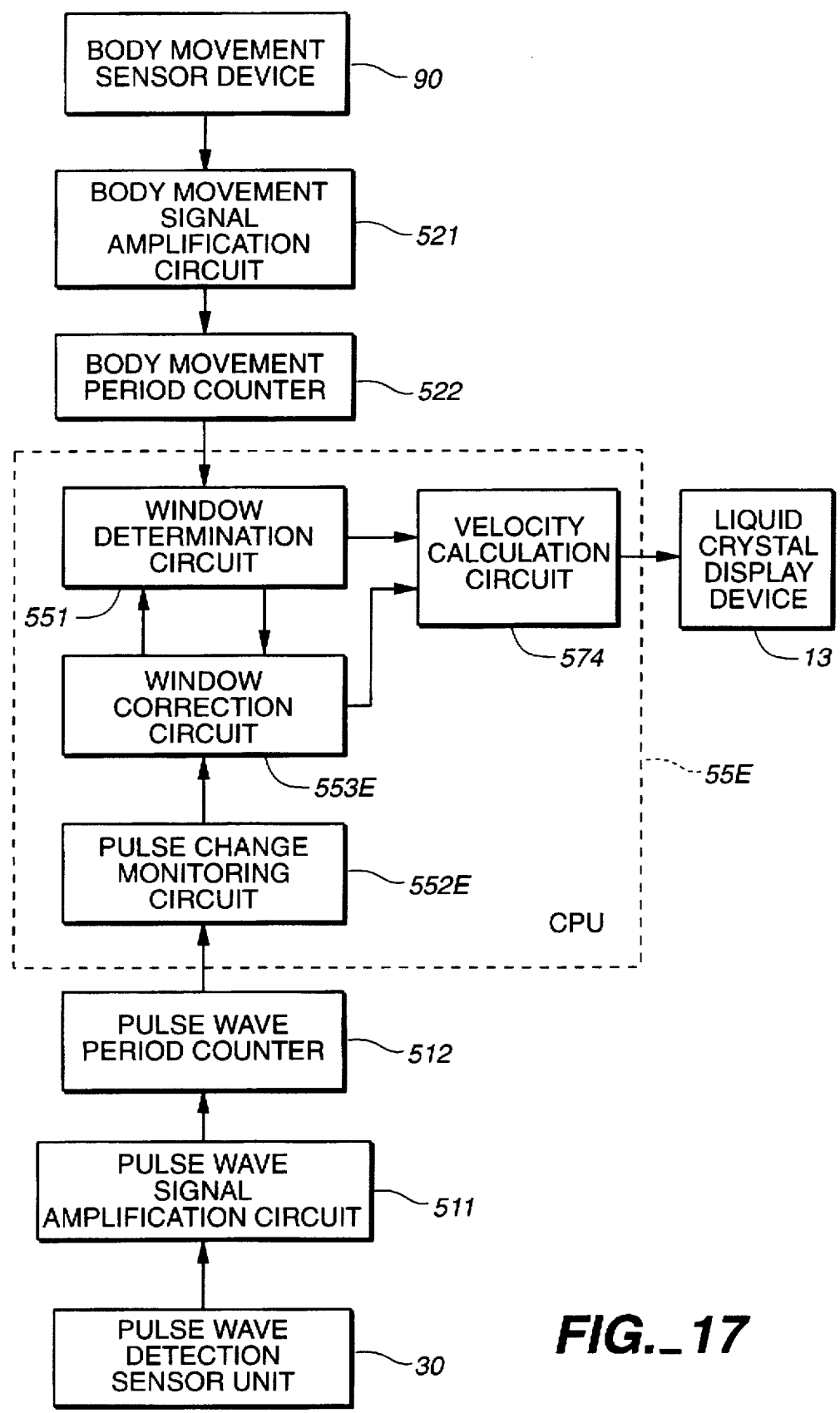
FIG._17

PERIOD AND FREQUENCY MEASUREMENT DEVICE WITH CORRECTION DEVICE AND METHOD THEREOF

BACKGROUND OF THE INVENTION

Field of the Invention

The invention relates to a period and frequency measurement device used for measuring a person's pulse and velocity based on pulse signals and body movement signals detected by sensor means. More specifically, the invention relates to a technology for determining valid measurements by optimizing a range or window for pulse rate and velocity.

Description of the Related Art

Devices, which are typically worn on a person's wrist, are known which can measure a person's pulse and velocity during exercise or movement. The blood pressure pulse and velocity are based on measures of pulse waves and body movements using sensors. However, error in data may occur in measuring these parameters due to a variety of reasons. Inclusion of these erroneous values in the determination of the user's or subject's condition can lead to the wrong result. Typically, this kind of measurement device uses as a reference value, such as the previously taken measurement value or the average of several measurement values taken immediately before as discussed in Japanese patent Publication No. 63-34731, multiplies this reference value by certain coefficients to set upper and lower margins, such a conventional device then determines whether the current measurement value is normal based on whether or not it is within the range or window defined by these upper and lower margins.

However in such conventional devices, a problem exists if a window is set up by merely multiplying the previous measurement (reference value) by certain coefficients to obtain upper and lower margins, as in conventional methods. That is, a normal value can be differentiated from an abnormal value fairly accurately if changes in body movement are small, such as when the subject is at rest. However, because the pulse rate changes dramatically at the beginning of exercise, window correction cannot keep up with this degree of change. For example, in FIG. 18, the horizontal and vertical axes show elapsed time and pulse rate, respectively, and the change in pulse rate over time, before and after exercise, is plotted as polygonal line P. In this figure, window correction can keep up with the pulse rate change before the start of exercise (before time t1), but cannot keep up with the changes immediately after the start of exercise (immediately after time t1) due to the significant increase in pulse rate. Consequently, even if the measurement taken at this time is normal, it will be eliminated as being abnormal. As a result, such a value will not be displayed and window correction can never occur as long as such a value is judged to be abnormal.

Conversely, widening the window too far, in an attempt to improve response to changes in pulse rate, will defeat the original purpose of eliminating abnormal values.

These problems are also encountered by devices that measure running velocity which exhibits the same changes as pulse rate.

OBJECTS OF THE INVENTION

Therefore, it is an object of the present invention is to solve the abovementioned problems.

It is another object of the present invention to provide a period and frequency measurement device that produces an appropriate window by varying the window to follow the changes, even if pulse rate and velocity change dramatically.

SUMMARY OF THE INVENTION

According to an aspect of the present invention, a device is provided for measuring pulse rate, by first, setting an upper margin of the window for the measurement result at 20% larger than the previous measurement value and the lower margin at 20% smaller than the previous measurement value. Subsequently, when body movements become larger, for the following 4 seconds, the upper margin is widened by 80% from the previous measurement value and the lower margin is narrowed by 10%. From then on, the upper margin is narrowed to +60%, +40%, and +20%. Note that if body movements become smaller, the upper margin is widened by 10% from the previous measurement value while the lower margin is set at −60% of the previous measurement value.

In order to solve the above-mentioned problems, the period and frequency measurement device related to this invention comprises a sensor means for measuring pulse waves and body movement. A window determination means sets a reference value based on the measurements previously taken by the sensor means (the previous measurement value itself or multiple measurement values taken including the previous measurement value) and determines whether or not the current measurement value taken by the sensor means falls within the window defined by the upper and lower margins relative to the reference value. A window correction means that corrects the window to be used for the next measurement value to be taken by the sensor means, applies a specified correction to the current measurement value if the determination result of the window determination means indicates that the current measurement value taken by the sensor means falls outside the current window.

In other words, the period and frequency measurement device according to the invention solves the above-mentioned problems by changing the reference value of the window when the period and frequency signals of pulse waves and body movement fall outside the specified range (window), and instead of eliminating and ignoring rapid changes in period and frequency of pulse waves and body movement as abnormal signals, corrects the window based on the measurement value. Therefore, appropriate window determination can be made because the window follows large changes in pulse waves and body movement.

In this invention, the window correction means is preferably configured such that it increments the current measurement value and uses the result as a new reference value if the determination result of the window determination means indicates that the current measurement value exceeds the upper margin of the window; and such that it decrements the current measurement value and uses the result as a new reference value if the determination result of the window determination means indicates that the current measurement value falls below the lower margin of the window.

With such a configuration, if rapid changes occur in the period and frequency of the signal, the next measurement will be taken after the window correction means shifts the window based on the degree to which the signal deviates from the window (e.g., over the upper margin or below the lower margin). Therefore, even if period and frequency change dramatically, the excellent follow-up characteristic of the window allows the window to be correctly determined.

The invention may comprise a calculation means that calculates status values such as pulse rate and velocity based on the current measurement values if the determination result of the window determination means indicates that the current measurement values taken by the sensor means fall within the window, and that calculates status values such as pulse rate and velocity based on the reference values generated from the measurement values by the window correction means if the determination result of the window determination means indicates that the current measurement values taken by the sensor means fall outside the window; and a display means that displays status values such as pulse rate and velocity calculated by the calculation means.

Here, the upper and lower margins may be set to be equal, in which case the reference value becomes the center value of the window.

The period and frequency measurement device according to another aspect of the present invention comprises a body movement detection sensor means for sensing body movement and a pulse wave detection sensor means for sensing pulse waves. A window determination means sets a reference value based on the measurements taken previously by either the pulse wave detection sensor means or the body movement detection sensor means (the previous measurement value itself or multiple measurement values taken including the previous measurement value) and determines whether or not the current measurement value taken by one of the sensor means falls within the window defined by the upper and lower margins relative to the reference value. A change monitoring means monitors the change in -the measurement value taken by the other sensor means. A window correction means corrects the window to be used for the current measurement value or the next measurement value to be taken by one of the sensor means, based on the monitoring result of the change monitoring means. In other words, this embodiment is characterized in that window correction is performed based on the measurement value taken by another sensor means.

In this aspect, when the pulse wave detection sensor means is used as one of the sensor means, the period and frequency measurement device is configured as a pulse rate counter; and in such a configuration, the other sensor means is the body movement detection sensor means, and the change monitoring means is a body movement change monitoring means that monitors body movement changes based on the measurement values taken by the body movement detection sensor means. If the configuration is reversed as will be described below, the period and frequency measurement device is configured as a velocity counter.

In this invention, the window correction means can be configured such that it corrects the window for the next measurement value to be taken by the pulse wave detection sensor means, by incrementing the current measurement value taken by the pulse wave detection sensor means and using the result as a new reference value if the determination result of the window determination means indicates that the current measurement value taken by the pulse wave detection sensor means falls outside the window and if the monitoring result of the body movement change monitoring means shows that body movement has increased; and by decrementing the current measurement value taken by the pulse wave detection sensor means and using the result as a new reference value if the determination result of the window determination means indicates that the current measurement value taken by the pulse wave detection sensor means falls outside the window and if the monitoring result of the body movement change monitoring means shows that body movement has decreased.

With such a configuration, the direction and magnitude of window reference value correction can be optimized by forecasting a rising or falling pulse rate trend based on body movement changes. Therefore, even at the start and finish of exercise or during a significant velocity change when pulse rate changes are temporarily large, the window can be appropriately corrected to follow those changes.

Furthermore, the invention may comprise a pulse rate calculation means that calculates pulse rate based on the current measurement value if the determination result of the window determination means indicates that the current measurement value taken by the pulse wave detection sensor means falls within the window, and that calculates pulse rate based on the reference value generated from the measurement values by the window correction means if the determination result of the window determination means indicates that the current measurement value taken by the pulse wave detection sensor means falls outside the window; and a display means that displays the pulse rate calculated by the pulse rate calculation means.

In this invention, the window correction means is preferably configured such that it makes corrections in proportion to the difference between body movement, determined based on the monitoring result of the body movement change monitoring means, and the current measurement value taken by the pulse wave detection sensor means.

Here again, the upper and lower margins may be set to be equal, in which case the reference value becomes the center value of the window.

In this invention, another window correction means can be configured such that it corrects the window to be used for the current measurement value or the next measurement value to be taken by the pulse wave detection sensor means, by performing the first correction, i.e., widening the upper margin, if the monitoring result of the body movement change monitoring means indicates increased body movement, and by performing the second correction, i.e., widening the lower margin, if the monitoring result of the body movement change monitoring means indicates decreased body movement.

With such a configuration, even when pulse rate changes drastically, window correction can sufficiently keep up with those changes because, by matching the body movement changes and pulse changes in an actual pattern, the upper margin of the window for pulse rate is widened as the first correction, when increased body movement is expected to accelerate the pulse; and the lower margin of the window for pulse rate is widened as the second correction, when decreased body movement is expected to decelerate the pulse. Therefore, the window can be appropriately determined.

In this case, the window correction means preferably makes the upper margin widest in the first correction, immediately after body movement increases, and subsequently returns the upper margin to the pre-correction state as time passes.

Furthermore, the window correction means is preferably configured such that it narrows the lower margin in the first correction, immediately after body movement increases; and narrows the upper margin in the second correction, immediately after body movement decreases.

Additionally, the window correction means is preferably configured such that it performs the first correction if the monitoring result of the body movement change monitoring means indicates increased body movement and if the previous or the current measurement value taken by the pulse wave detection sensor means is less than a specified value, and performs the second correction if the monitoring result of the body movement change monitoring means indicates decreased body movement and if the previous or the current measurement value taken by the pulse wave detection sensor means is greater than a specified value.

If the configuration of the invention is reversed such that one of the sensor means is the body movement detection sensor means, the period and frequency measurement device is configured as a velocity counter. In this case, the other sensor means is the pulse wave detection sensor means, and the change monitoring means is a pulse change monitoring means that monitors pulse changes based on the measurement values taken by the pulse wave detection sensor means.

In this case again, the window correction means can be configured such that it corrects the window for the next measurement value to be taken by the body movement detection sensor means, by incrementing the current measurement value taken by the body movement detection sensor means and using the result as a new reference value if the determination result of the window determination means indicates that the current measurement value taken by the body movement detection sensor means falls outside the window and if the monitoring result of the pulse change monitoring means shows that the pulse rate has accelerated; and by decrementing the current measurement value taken by the body movement detection sensor means and using the result as a new reference value if the determination result of the window determination means indicates that the current measurement value taken by the body movement detection sensor means falls outside the window and if the monitoring result by the pulse change monitoring means shows that the pulse rate has decelerated.

With such a configuration, the direction and magnitude of window reference value correction can be optimized by forecasting a rising or falling velocity trend based on pulse changes. Therefore, even at the start and finish of exercising, or when velocity count changes are temporarily large, the window can be appropriately corrected to follow those changes.

Furthermore, the invention preferably comprises a velocity calculation means that calculates velocity based on the current measurement value if the determination result of the window determination means indicates that the current measurement value taken by the body movement detection sensor means falls within the window, and that calculates velocity based on the reference value generated from the measurement value by the window correction means if the current measurement value taken by the body movement detection sensor means falls outside the window; and a display means that displays the velocity calculated by the velocity calculation means.

The window correction means is preferably configured such that it makes corrections in proportion to the difference between the pulse, determined based on the monitoring result of the pulse change monitoring means, and the current measurement value taken by the body movement detection sensor means.

In this case again, the upper and lower margins may be set to be equal, in which case the reference value becomes the center value of the window.

In this invention, another window correction means can be configured such that it corrects the window to be used for the current measurement value or the next measurement value to be taken by the body movement detection sensor means, by performing the first correction, i.e., widening the upper margin, if the monitoring result of the pulse wave change monitoring means indicates a faster pulse, and by performing the second correction, i.e., widening the lower margin, if the monitoring result of the pulse wave change monitoring means indicates a slower pulse.

With such a configuration, even when velocity changes drastically, window correction can sufficiently keep up with those changes because, by matching the body movement and pulse changes of an actual pattern, the upper margin of the window for velocity is widened as the first correction, when a faster pulse is expected to raise the velocity; and the lower margin of the window for velocity is widened as the second correction, when a slower pulse is expected to lower the velocity. Therefore, the window can be appropriately determined.

In this case, the window correction means preferably makes the upper margin widest in the first correction, immediately after the pulse rate accelerates, and subsequently returns the upper margin to the pre-correction state as time passes.

Furthermore, the window correction means is preferably configured such that it narrows the lower margin in the first correction, immediately after the pulse rate accelerates; and narrows the upper margin, in the second correction, immediately after the pulse decelerates.

Additionally, the window correction means is preferably configured such that it performs the first correction if the monitoring result of the pulse wave change monitoring means indicates a faster pulse and if the previous or the current measurement value taken by the body movement detection sensor means is less than a specified value, and performs the second correction if the monitoring result of the pulse wave change monitoring means indicates a slower pulse and if the previous or the current measurement value taken by the body movement detection sensor means is greater than a specified value.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts.

FIGS. 1A and 1B are diagrams showing the overall configuration and application of the period and frequency measurement device in accordance with the present invention;

FIG. 2 is a top view of the main body of the measurement device shown in FIG. 1;

FIG. 3 is a side view of the main body the period and frequency measurement device shown in FIG. 1, viewed from the 3 o'clock direction thereof;

FIG. 4 a detailed cross-sectional view of the sensor unit used in the period and frequency measurement device shown in FIG. 1;

FIG. 5 is a diagram showing the configuration of the sensor and control circuit of the period and frequency measurement device in accordance with a first embodiment of the present invention;

FIG. 6 is a functional block diagram showing the functions of a processor used in the control function of the device shown in FIG. 5;

FIG. 7 is a flow chart showing the window correction process for the pulse rate measurement performed by the period and frequency measurement device shown in FIG. 5;

FIG. 8 is a diagram showing the window correction performed by the period and frequency measurement device shown in FIG. 5;

FIG. 9 is a schematic diagram showing the configuration of the sensor and control circuit of the period and frequency measurement device in accordance with a second embodiment of the present invention;

FIG. 10 is a block diagram showing the functions of a processor used in the control circuit of the period and frequency measurement device shown in FIG. 9;

FIGS. 11, 11A and 11B are flow charts showing the window correction process for the pulse rate measurement performed by the period and frequency measurement device shown in FIG. 9;

FIG. 12 is a block diagram showing the functions of a processor used in the control circuit of the period and frequency measurement device in accordance with a third embodiment of the present invention;

FIG. 13 is a diagram showing the configuration of the sensor and control circuit of the period and frequency measurement device in accordance with a fourth embodiment of the present invention;

FIG. 14 is a block diagram showing the functions of a processor used in the control circuit of the period and frequency measurement device shown in FIG. 13;

FIGS. 15, 15A and 15B are flow charts showing the window correction process for pulse rate measurement performed by the period and frequency measurement device shown in FIG. 13;

FIGS. 16A–16C are diagrams showing the window correction performed by the period and frequency measurement device shown in FIG. 13;

FIG. 17 is a block diagram showing the functions of a processor used in the control circuit of the period and frequency measurement device in accordance with a fifth embodiment of the present invention; and FIG. 18 is diagram showing a conventional window correction method.

DESCRIPTION OF THE PREFERRED EMBODIMENTS

The present invention is explained with references to the accompanying drawings.

FIGS. 1A and 1B show the configuration of the period and frequency measurement device in accordance with the present invention.

In FIGS. 1A and 1B, the configuration of the period and frequency measurement device 1 (pulse rate counter/portable pulse wave measurement device) of the present invention primarily comprises device main body 10 possessing a wristwatch structure, cable 20 connected to this device main body 10, and pulse wave detection sensor unit 30 (pulse wave measurement sensor means) installed at the end of cable 20. The end of cable 20 is provided with connector piece 80 which is secured detachably to connector circuit 70 provided on the 6 o'clock side of device main body 10. Wristband 12, which is wrapped around the wrist from the 12 o'clock direction of the wristwatch and fastened in the 6 o'clock direction, is installed in device main body 10. Wristband 12 allows device main body 10 to be easily put on or taken off from the wrist. Referring specifically to FIG. 1B, pulse wave detection sensor unit 30 is attached to the area between the base and the first joint of the index finger and is shielded from ambient light by strap 40. Attaching pulse wave detection sensor unit 30 to the base of a finger in this way keeps cable 20 short and prevents it from getting in the way during running or other exercise. Furthermore, taking into consideration the temperature distribution between the palm and finger tip in cold weather, the temperature at the finger tip tends to decrease substantially while the temperature at the base of the finger decreases relatively little. Therefore, attaching pulse wave detection sensor unit 30 at the base of the finger enables pulse rate (status value) to be accurately measured even during outdoor exercise on a cold day.

CONFIGURATION OF THE DEVICE MAIN BODY

FIG. 2 is a top view showing main body device 10 of the period and frequency measurement device of the present invention, with the wristband and cable removed; FIG. 3 is a side view of this period and frequency measurement device, viewed from the 3 o'clock direction.

In FIG. 2, device main body 10 is provided with watch case 11 or body case preferably made of a suitable material such as plastic or metal. The top side of watch case 11 is provided with liquid crystal display device 13 (display device) with, an example, an electroluminescent (EL) backlight for displaying various parameters such as running time, velocity during walking, and pulse wave information such as pulse rate, in addition to current time and date. Liquid crystal display device 13 is provided with first segment display circuit 131 positioned on the upper left side of the display surface, second segment display circuit 132 positioned on the upper right side of the display surface, third segment display circuit 133 positioned on the lower right side of the display surface, and dot display circuit 134 which can graphically display various types of information positioned on the lower left side of the display.

Control circuit 5, which performs various types of control and data processing in order to determine the change in pulse rate based on the pulse wave signal measured by pulse wave detection sensor unit 30 and to display the result on liquid crystal display device 13, is provided inside watch case 11. Control circuit 5 is also provided with a timing circuit, and thus can display normal time, lap time, split time, etc. on liquid crystal display device 13.

Button switches 111 through 115, which are used for external operations, such as, time adjustment and display mode switching, are provided on the perimeter of watch case 11. Additionally, larger button switches 116 and 117 are provided on the surface of the watch case. Switch 116 controls the lap timing and switch 177 toggles the starting and stopping of measurement.

Battery 59, preferably button-shaped contained inside watch case 11, is installed in period and frequency measurement device 1, and cable 20 supplies electrical power from battery 59 to pulse wave detection sensor unit 30, cable 20 also providing communication from the pulse wave detection sensor unit 30 to control circuit 5 of device main body 10.

Device main body 10 also contains body movement sensor device 90 (body movement detection sensor means) which utilities acceleration sensor 91 to detect body movement.

The size of device main body 10 must generally be increased as more functions are added to period and frequency measurement device 1. However, device main body 10 cannot be extended in the 6 or 12 o'clock directions of the watch because it must be worn around a wrist. Therefore, device main body 10 uses watch case 11 which is longer in the 3 and 9 o'clock directions than in the 6 and 12 o'clock directions. However, wristband 12 is connected eccentrically toward the 3 o'clock side, leaving extended circuit 101 in the 9 o'clock direction, viewed from wristband 12, but no such extended circuit in the 3 o'clock direction. Consequently, this structure, despite the use of long watch case 11, allows free wrist movement and eliminates the possibility of the back of the hand striking watch case 11.

An alarm or annunciator, such as flat piezoelectric element 58, is positioned in the 9 o'clock direction, viewed from battery 59, inside watch case 11. Since battery 59 is heavier than piezoelectric element 58, the center of gravity of device main body 10 is positioned eccentrically in the 3 o'clock direction. Wristband 12 is connected to the side on which the center of gravity is located, as such device main body 10 can be securely attached to the wrist. Furthermore, the positioning of battery 59 and piezoelectric element 58 in the planar direction allows device main body 10 to be thinly constructed. Battery cover 118 installed on the back side as shown in FIG. 3 allows the user to easily replace battery 59.

Structure for attaching the device main body to the wrist

In FIG. 3, connecting circuit 105 for holding stopping pin 121 installed on the end of wristband 12 is formed in the 12 o'clock direction of watch case 11. Receiving circuit 106 is provided in the 6 o'clock direction of watch case 11, and the receiving circuit 106 is provided with fastener 122 for securing in place the middle point of wristband 12 wound around the wrist, in the longitudinal direction of the band.

In the 6 o'clock direction of device main body 10, the circuit from bottom surface 119 to receiving circuit 106 is formed as an integral part of watch case 11 and forms rotation stop circuit 108 which is positioned at approximately 1150 from bottom surface 119. That is, when wristband 12 is used to attach device main body 10 to top circuit L1 (side of the back of the hand) of right wrist L (arm), bottom surface 119 of watch case 11 tightly contacts top circuit L1 of wrist L while rotation stop circuit 108 contacts side circuit L2 where radius R is located. In this state, bottom surface 119 of device main body 10 more or less straddles radius R and ulna U, of wrist L while rotation stop circuit 108 and the circuit between bent circuit 109 of bottom surface 119 and rotation stop circuit 108 contact radius R. Because rotation stop circuit 108 and bottom surface 119 form an anatomically ideal angle of approximately 115° as explained above, device main body 10 tends not twist or turn around arm L even if an attempt is made to turn it in the direction of arrows A or B. Furthermore, because the rotation of device main body 10 is restricted only in two locations on the side of the arm by bottom surface 119 and rotation stop circuit 108, bottom surface 119 and rotation stop circuit 108 securely contact the arm even if it is thin, and provide a secure rotation stopping effect and comfortable fit even if the arm is thick.

Configuration of the pulse wave detection sensor unit

FIG. 4 shows a cross-sectional view of the pulse wave detection sensor unit of the present invention.

In this figure, component housing space 300 is formed between the casing of pulse wave detection sensor unit 30 and bottom lid 302 on the bottom side of sensor frame 36. Circuit board 35 is positioned inside component housing space 300. LED 31, phototransistor 32, and other electronic components are mounted on circuit board 35. One end of cable 20 is fastened to pulse wave detection sensor unit 30 by bushing 393, and various wires of cable 20 are secured, by for example soldering, to various wirings or patterns on circuit board 35. Pulse wave detection sensor unit 30 is attached to the finger such that cable 20 is extended from the base of the finger toward device main body 10. LED 31 and phototransistor 32 are arranged along the length of the finger, with LED 31 positioned on the finger tip side and phototransistor 32 positioned at the base of the finger. This configuration provides the effect of making it difficult for the ambient light to impinge phototransistor 32.

In pulse wave detection sensor unit 30, a light transmission window is formed by translucent plate 34 which is made of a glass plate on the upper circuit of sensor frame 36, and the light-emitting surface and light-receiving surface of LED 31 and phototransistor 32, respectively, are oriented toward the translucent plate 34. Because of such a configuration, when a finger surface is pressed onto external surface 341 of translucent plate 34, LED 31 emits light toward the finger surface and phototransistor 32 can receive part of the light emitted by LED 31 that is reflected by the finger. Note that external surface 341 of translucent plate 34 protrudes farther than surrounding circuit 361 in order to improve its contact with the finger surface.

In this working example, an InGaN (indium-gallium-nitrogen) blue LED is preferably used as LED 31, and its emission spectrum possesses a peak amplitude at 450 nm and its emission wavelength ranges from 350 to 600 nm. To match with LED 31 possessing such characteristics, a GaAsP (gallium-arsenic-phosphorus) phototransistor is preferably used as phototransistor 32, and the light-receiving wavelength of the element itself ranges from 300 to 600 nm, with some sensitive circuits also at or below 300 nm.

When pulse wave detection sensor unit 30 thus configured is attached to the base of the finger by sensor-fastening strap 40 and light is emitted from LED 31 toward the finger, the light reaches blood vessels, and part of the light is absorbed by hemoglobin in the blood and part of it is reflected. The light reflected by the finger (blood) is received by phototransistor 32, and the change in the amount of received light corresponds to the change in the blood volume (pulse wave in the blood). That is, because the reflected light becomes weak when the blood volume is high and becomes strong when the blood volume is low, data such as pulse rate can be measured by optically detecting the intensity of the reflected light as a pulse wave signal.

The present invention uses LED 31 with an emission wavelength range of between 350 and 600 nm and phototransistor 32 with a light-receiving wavelength range of between 300 and 600 nm, and vital information is displayed based on the results taken in the overlapping wavelengths of between approximately 300 and approximately 600 nm, i.e., wavelengths of approximately 700 nm or shorter. When such pulse wave detection sensor unit 30 is used, even if the ambient light strikes the exposed part of the finger, lights with wavelengths of 700 nm or shorter contained in the ambient light do not use the finger as a light guide to reach phototransistor 32 (light-receiving circuit). The reason for this is as follows, since lights with wavelengths of 700 nm or shorter contained in the ambient light do not easily penetrate the finger, the ambient light reaching the circuit of the finger not covered by the sensor fastening strap 40 will not penetrate the finger to reach phototransistor 32. In contrast, if an LED possessing an emission peak at around 880 nm and a silicon phototransistor are used, a light-receiving wavelength range of between 350 and 1,200 nm will result. In such a case, changes in the ambient light level tend to cause measurement errors because pulse waves will be detected using a light with 1 mm wavelength which can use the finger as a light guide to easily reach phototransistor 32.

Furthermore, because pulse wave information is obtained using lights with approximately 700 nm or shorter wavelengths, the S/N ratio of the pulse wave signal based on blood volume change is high. The reason for this is as follows. The absorption coefficient of hemoglobin in the blood for lights with wavelengths of between 300 and 700 nm is several times to approximately one hundred or more times larger than the absorption coefficient for a light with wavelength of 800 nm which has been conventionally used as the detection light. As a result, lights with wavelengths of between 300 and 700 nm change sensitively to blood volume changes, producing higher pulse wave detection rate (S/N ratio) based on blood volume change.

First Embodiment

Configuration of the control circuit

FIG. 5 shows the configurations of individual sensors and control circuit 5. In pulse wave detection sensor unit 30, the light emitted from LED 31 passes into the body and the reflected light is modulated according to the volume change in the blood vessel, and after the resulting optical change is converted to an electrical current by phototransistor 32, a voltage output (pulse wave signal) is obtained by collector resistor R1. Pulse wave signal amplification circuit 511 comprising three stages (an AC amplifier A (stage 1), a low pass filter LPF (stage 2), and a Stemmata trigger comparator for square wave conversion TR (stage 3)) is provided in communication with pulse wave detection sensor unit 30, and pulse wave period counter 512 is provided in communication amplification circuit 511. Based on the clock signal from reference clock 550, pulse wave period counter 512 measures the time between the edges of square waves that are output from pulse wave signal amplification circuit 511, and outputs the counter value K to processor 55A. Processor 55A maybe implemented as a microprocessor or any other suitable discrete components.

The instructions for controlling processor 55A are stored in non-volatile memory. Processor 55A performs calculations, using RAM 562 as the operation memory based on the clock signal from reference clock 550, on liquid crystal display device 13.

FIG. 6 is a block diagram showing the functions of processor 55A. As is evident from this figure, the output of pulse wave detection sensor unit 30 is detected and amplified by pulse wave signal amplification circuit 511, and the period is counted by pulse wave period counter 512 which is a period counting means. The output of the pulse wave period counter 512 is analyzed to determine whether its valve is within the specified window by window determination function or circuit 551 (window determination means) provided in processor 55A. Here, the window is defined by predetermined upper and lower margins relative to the reference value determined based on the previous measurement value. In the first embodiment, the reference value is equivalent to the center value because the upper and lower margins are equal.

If window determination function 551 indicates that the current output (current measurement value) of pulse wave period counter 512 falls within the window, this value is sent to pulse rate calculation circuit 554 (pulse rate calculation means) without any modification. Pulse rate calculation function 554 converts the period that is output by pulse wave period counter 512 to pulse rate, and the resulting value is display as a pulse rate on liquid crystal displayed device 13.

In contrast, if the current output (current measurement value) of pulse wave period counter 512 falls outside the window, that value is then corrected by window correction function 553A (window correction means) and is sent to pulse rate calculation circuit 554. Therefore, pulse rate calculation function 554 converts the output of pulse wave period counter 512 that has been corrected by window correction function 553A to a pulse rate, and the resulting value is display as a pulse rate on liquid crystal display device 13.

Furthermore, if the current output (current measurement value) of pulse wave period counter 512 falls outside the window, this value is corrected by window correction function 553A, and thus window correction function 553A is in effect correcting the center value of the window for the next measurement result.

The method of processing measurement results will be explained in detail with reference to the flow chart in FIG. 7.

First, $S_{old}$ which becomes the center value of the next window determination is calculated based on counter value K fetched from pulse wave period counter 512 (step ST601). The actual measurement now begins, and after calculating pulse period S by fetching counter value K of pulse wave period counter 512 again (step ST602), window determination function 551 calculates the lower margin Low which is 20% lower than window determination reference value $S_{old}$ and upper margin High which is 20% higher than reference value $S_{old}$ (steps ST603 and ST604). Note that because pulse wave period and pulse rate are different in dimension, upper margin High and lower margin Low correspond to the lower and upper margins of the pulse rate window, respectively.

Next, it is determined whether or not the current measurement of period S falls within the window defined by lower margin Low and upper margin High (steps ST605 and ST606). These steps are performed by window determination function 551 (window determination means).

If pulse wave period S is below the window width, a value that is 2% smaller than the window determination reference value $S_{old}$ (center value) is used as the next reference value $S_{old}$ (step ST607). In contrast, if pulse wave period S is above the window width, a value that is 2% larger than the window determination reference value $S_{old}$ (center value) is used as the next reference value $S_{old}$ (step ST608).

Window correction function 553A (window correction means) in effect performs window correction for the next measurement value as explained below, because it corrects reference value $S_{old}$ based on the window determination result for the current measurement value as described above.

Next, if period S is within the window, this period S is assigned to pulse rate calculation variable T as is (step ST609), and if period S is outside the window, a corrected reference value $S_{old}$ is assigned to pulse rate calculation variable T (step ST610). Next, pulse rate calculation variable T is converted to pulse rate M in step ST611. These steps are performed by pulse rate calculation function 554 (pulse rate calculation means).

Next, in step ST612, window correction for the next measurement value is performed by assigning pulse rate calculation variable T to reference value $S_{old}$ for the next window determination.

Then in step ST613, an instruction is issued for displaying a pulse rate on liquid crystal display device 13, and pulse rate M is displayed on liquid crystal display device 13.

The steps so far described constitute one period, and the steps beginning with ST602 are repeated for the next measurement and display.

FIG. 8 shows an example of measuring pulse rate using such a processing method under a condition involving rapid pulse rate changes, such as during exercise. In this figure, the horizontal and vertical axes show elapsed time and pulse rate, respectively. Here, $M_n$ (where n is an integer) indicates each pulse rate measurement value, which results when pulse wave period $S_n$ obtained by the average pulse rate period calculation routine is converted to pulse rate.

First, reference value $S_{old}$ (center value) and the window width (the range indicated by the up and down arrows in the figure) are determined by the initial value $M_0$. In FIG. 8, period $S_n$ and reference value $S_{old}$ are shown as $M_n$ and $M_{old}$ after conversion to a pulse rate, in order to maintain dimensional consistency.

Next, if measurement value $M_1$ is within the window possessing value $M_{old}$ as its center, measurement value $M_1$ is displayed as is, and the reference value (window center value) for the next window is set based on measurement value $M_1$. The same steps are taken for $M_2$ measured subsequently. In this example, exercise was started after measurement value $M_2$ was obtained but before measurement value $M_3$ was obtained, resulting in a rapid increase in pulse rate.

If value $M_3$ measured falls outside the window, reference value $M_{old}$ of the window is corrected upward, and a corrected value is displayed. Furthermore, this corrected value is set as the reference value (window center value) for the next window. Although measurement values $M_4$, $M_5$, and $M_6$ are also outside the window, reference value $M_{old}$ of the window is gradually corrected, and as a result measurement value $M_7$ falls inside the window. Therefore, unless the pulse rate changes abruptly at a later time, the true pulse rate (where Mn falls inside the window) can be displayed.

Although it is possible that the pulse rate will fluctuate according to a different pattern, normal pulse rate stays within a certain range, i.e., the lower limit of pulse rate ranges between 30 and 100 pulses/minute and the upper limit between 150 and 240 pulses/minute, and thus window reference value (center value) correction can always keep up with pulse rate changes, and the pulse rate eventually falls within an appropriate zone. Therefore, although a reading containing an error will be temporarily displayed when the pulse rate changes rapidly, the erroneous display is not locked in and the duration of the erroneous display can be minimized. In conclusion, in this example, abnormal values can be eliminated from period measurement and at the same time the window can follow rapid changes in measurement values.

It is of course possible to display "ERROR" when a measurement value is outside the window, to clearly indicate that the pulse rate obtained is not true. Furthermore, although pulse rate was obtained in this example, it is possible to obtain, in which case a similar process can be applied to the measurement results of body movement sensor device 90 instead of pulse wave detection sensor unit 30.

Second Embodiment

The configuration of the period and frequency measurement device in the second embodiment is substantially similar to that of the first embodiment. Accordingly, the same symbols are used to represent the same elements and their detailed explanations are omitted.

FIG. 9 shows the configurations of individual sensors and control circuit 5 of period and frequency measurement device 1 of the second embodiment. In pulse wave detection sensor unit 30, similar to the first embodiment, the light emitted from LED 31 passes into the body and the reflected light is modulated according to the volume change in the blood vessel, and after the resulting optical change is converted to electrical current by phototransistor 32, a voltage output (pulse wave signal) is obtained by a collector resistor R1. Pulse wave signal amplification circuit 511 is in communication with pulse wave detection sensor unit 30, and pulse wave period counter 512 is in communication amplification circuit 511. In accordance with the clock signal from reference clock 550, pulse wave period counter 512 measures the time between the edges of square waves that are output from pulse wave signal amplification circuit 511, and outputs the counter value K to processor 55B.

The second embodiment further comprises body movement sensor device 90. Body movement sensor device 90 comprises a pre-amplifier consisting of acceleration sensor 91 which acts as a body movement sensor, a discharging resistor $R_d$ field effect transistor (FET) T1. Body movement signal amplification circuit 521 comprises an AC amplifier A2, a low pass filter LPF2, and a Stemmata trigger comparator TR2 for square wave conversion is also provided behind body movement sensor device 90, and body movement period counter 522 is provided in communication with amplification circuit 521. Based on the clock signal from reference clock 550, body movement period counter 522 measures the time between edges of square waves that are output from body movement signal amplification circuit 521, and outputs the counter value T to processor 55B.

Instructions for processor 55B are stored in ROM 561. Processor 55B performs calculations using RAM 562 as the operation memory in accordance with the program stored in ROM 561 and the clock signal from reference clock 550 processor 55B, and displays the calculation result (pulse rate) on liquid crystal display device 13.

FIG. 10 is a block diagram showing the functions of processor 55B. The output of pulse wave detection sensor unit 30 is detected and amplified by pulse wave signal amplification circuit 511, and the period is counted by pulse wave period counter 512. Window determination circuit 551 provided in CPU55B determines whether or not the output pulse wave period counter 512 falls within the specified window. Here, the window is defined by certain upper and lower margins relative to the reference value determined based on the previous measurement value. In the second embodiment, the reference value is equivalent to the center value because the upper and lower margins are equal.

If the window determination result indicates that the current measurement value falls within the window, this value is sent to pulse rate calculation function or circuit 554 as is. In contrast, if the current output value falls outside the window, the current value is corrected by window correction function or circuit 553B (window correction means).

As noted above this configuration in the second embodiment is substantially similar to that of the first embodiment and detailed explanations will be omitted. The main feature of the second embodiment is that window correction function 553B determines how to correct the current measurement value by measuring and detecting any changes in the body movement.

In other words, the output of body movement sensor device 90 is detected and amplified by body movement signal amplification circuit 521 and the period is measured by body movement period counter 522. The trend in body movements is determined based on this period, the resulting value is stored in body movement change monitoring memory 552B (body movement change monitoring means/ change trend storage means). Based on the change trend stored here, window correction function 553B determines by how much the reference value, which will become the center value of the window, should be increased or decreased.

The method of processing measurement results will be explained in detail with reference to the control flow chart in FIGS. 11, 11A and 11B.

Initially, $S_{old}$ which becomes the center value of the next window determination is calculated based on counter value K fetched from pulse wave period counter 512 (step ST901). The actual measurement now begins, and period S is determined by fetching counter value K of period counter 512 again (step ST902).

Next, body movement change monitoring function 552B (body movement change monitoring means) determines the change trend of body movement period. In this processing, count value T of body movement period counter 522 is stored in variable SM (step ST903). Next, three adjoining body movement period points ($SM_n$, $SM_{n-1}$, and $SM_{n-2}$) stored in RAM 562 are updated to the three points from SM stored above (steps ST904, ST905, and ST906). Next, the differences between $SM_{n-2}$ through $SM_n$ which change over time are determined, and the sum total of these differences, $D_{eff}$ is obtained (step ST907).

Next, based on the value of $D_{eff}$, correction magnitudes "up" and "down" are determined from the conversion table shown in Table 1 (step ST908).

| $D_{eff}$ | Up | Down |
| --- | --- | --- |
| <−200 | 0.01 | 0.08 |
| −200 to −100 | 0.01 | 0.04 |
| −100 to 100 | 0.02 | 0.02 |
| 100 to 200 | 0.04 | 0.01 |
| 200< | 0.08 | 0.01 |

Note that when the value of Deff is positive, it indicates that the body movement is increasing, i.e., the running velocity is accelerating. Consequently, the load on the heart increases, and as a result the pulse rate increases in most cases. Therefore, as shown in Table 1, the correction magnitude "up" is set larger when $D_{eff}$ is positive and as its absolute value increases. Conversely, when the value of $D_{eff}$ is negative, it indicates that the running velocity is decelerating or the subject has stopped. Consequently, the load on the heart decreases, and as a result the pulse rate decreases in most cases. Therefore, as shown in Table 1, the correction magnitude "down" is set larger when Deff is negative and as its absolute value increases.

With these settings, if the processing (steps ST909, ST910, ST911, and ST912) by window determination function 551 (window determination means) shows that the pulse rate falls below the window, reference value $S_{old}$ (center value) for the next window determination is corrected in step ST913. During this step, appropriate correction is made using a "down" value that is set based on an expected downward trend in the pulse rate. In contrast, if the pulse rate is above the window, reference value $S_{old}$ (center value) for the next window determination is corrected in step ST914 using an "up" value based on an expected upward trend in the pulse rate. Since such processing corrects reference value $S_{old}$ for the next measurement value, as explained below, it is equivalent to the processing by window correction circuit 553B (window correction means).

As in the first embodiment in the processing steps (ST915, ST916, and ST917) by pulse rate calculation function 554 (pulse rate calculation means), period S that has gone through the determination by window determination function 551 or the value $S_{old}$ that has been corrected by the correction process in window correction function 553B is converted to pulse rate M per minute (step ST917). Furthermore, in step ST918, pulse rate calculation variable T (period) is assigned to variable $S_{old}$ as the reference value of the next window.

Next, the pulse rate M that has been determined is displayed, and the next measurement is then taken (step ST919).

As explained above, in the second embodiment, the direction and amount of correction of the window reference value (center value) in window correction circuit 553B are optimized by forecasting the rising or falling trend of the pulse rate based on body movement changes, allowing pulse rate to be measured with excellent response characteristics even when the pulse rate temporarily changes rapidly, such as at the start or end of exercising, or when the fluctuates dramatically.

Third Embodiment

In the second embodiment, during displaying of a pulse rate, the change trend of body movement periods was determined for optimizing the amount of correction for the window. In contrast, in the third embodiment, the amount of correction needed when the body movement period (e.g., running velocity) deviates from the window is optimized based on the change trend of the pulse wave period. In other words the third embodiment utilizes the correlation between the change trend of the body movement period and the change trend of the pulse rate period. The third embodiment utilizes the fact that when the pulse rate is increasing, the velocity is also increasing; and when the pulse rate is decreasing, the velocity is also decreasing in most cases.

As shown in the block diagram in FIG. 12, the configuration necessary for such processing requires only that the functions or circuits for measuring pulse wave period (pulse rate) be replaced with the functions for measuring velocity (body movement), and thus only brief explanations will be provided on this configurations. Furthermore, because the details of the processing performed in this example are substantially the same as those shown in the flow chart in FIG. 11, except that the processing for pulse wave period (pulse rate) is replaced with that for velocity (body movement), their explanations are omitted.

In the example shown in FIG. 12, after the output of body movement sensor device 90 is amplified by body movement signal amplification circuit 521, edge-to-edge period is measured by body movement period counter 522. Likewise, after the output of pulse wave detection sensor unit 30 is amplified by pulse wave signal amplification circuit 511 edge-to-edge period is measured by pulse wave period counter 512. Next, the change trend of pulse period is calculated and stored by pulse change monitoring function 552C (pulse change monitoring means) provided in processor 55C. The period determined by body movement period counter 522 is judged to be normal or abnormal through window determination by window determination circuit 551; and if the body movement period falls within the window, the current measurement of body movement period is judged to be normal and is converted to a velocity by velocity calculation function or circuit 574 (velocity calculation means).

In contrast, if the current body movement period measured falls outside the window, window correction function 522C (window correction means) corrects the reference value (center value) for the next window determination. Note that the amount of correction to be made to the current measurement value is optimized based on the monitoring result of body movement change monitoring function 552C. Velocity calculation function 574 then converts the corrected reference value to a velocity.

The velocity thus calculated by velocity calculation function 574 is then displayed on liquid crystal display device 13.

Fourth Embodiment

The basic configuration of the period and frequency measurement device in the fourth embodiment is substantially the same as the first embodiment 1, the same symbols are used to represent the same functions and their explanations will be omitted.

Configuration of the control function

As shown in FIG. 13, the configurations of individual sensors and control function 5 of period and frequency measurement device 1 of this example are the same as those of the third example. That is, in pulse wave detection sensor unit 30, the light emitted from LED 31 passes into the body and the reflected light is modulated according to the volume change in the blood vessel, and after the resulting optical change is converted to electrical current by phototransistor 32, a voltage output (pulse wave signal) is obtained by a collector resistor R1. Pulse wave signal amplification circuit 511 comprising an AC amplifier A, a low pass filter LPF, and a Stemmata trigger TR comparator for square wave conversion provided in communication with pulse wave detection sensor unit 30, and pulse wave period counter 512 is provided in communication with amplification circuit 511. Based on the clock signal from reference clock 550, pulse wave period counter 512 measures the time between the edges of square waves that are output from pulse wave signal amplification circuit 511, and outputs the counter value K to processor 55D.

The fourth embodiment is also provided with body movement sensor device 90. Body movement signal amplification circuit 521 comprising an AC amplifier A2, a low pass filter LPF2, and a Stemmata trigger comparator TR2 for square wave conversion (represent by circuit 521 and body movement period counter 522 are provided in communication with the body movement sensor device 90. Based on the clock signal from reference clock 550, body movement period counter 522 also measures the time between edges of square waves that are output from body movement signal amplification circuit 521, and outputs the counter value T to processor 55D.

FIG. 14 is a block diagram showing the functions of processor 55D. Processor 55D is provided with window determination function 551 which sets a specified reference value based on the previous detection result of pulse wave detection sensor unit 30 and which determines whether or not the current detection result obtained by pulse wave detection sensor unit 30 falls within the effective window defined by the upper and lower margins relative to this reference value; and with pulse rate calculation function 554 which calculates pulse rate based on the detection result if the result of window determination function 551 indicates that the current detection result obtained by pulse wave detection sensor unit 30 falls within the window.

Processor 55D is also provided with body movement change monitoring function 552D (body movement change monitoring means) which monitors whether or not the body movement has increased, based on the detection result of body movement sensor device 90; and with window correction function 553D (window correction means) which performs the first correction, i.e., widening the upper margin of the window, if the monitoring result of body movement change monitoring means 552D indicates increased body movements, and subsequently performs the second correction, i.e., widening the lower margin, if the monitoring result of body movement change monitoring means 552D indicates decreased body movements.

Note that window correction circuit 553D is configured such that it makes the upper margin the widest in the first correction, immediately after body movement increases, and subsequently returns the upper margin to the precorrection state as time passes. Furthermore, window correction circuit 553D is configured such that it narrows the lower margin in the first correction, immediately after body movement increases, and narrows the upper margin, in the second correction, immediately after body movement decreases. Additionally, window correction circuit 553D is configured such that it performs the first correction when the monitoring result of body movement change monitoring means 552D indicates increased body movements and if the previous or the current pulse ate measurement is smaller than a specified value, and subsequently performs the second correction when the monitoring result of body movement change monitoring means 552D indicates decreased body movements and if the previous or the current pulse rate measurement is larger than a specified value.

Window determination and correction

Non-volatile memory or ROM 561 contains programs that correspond to pulse rate calculation function 554, window determination function 551, window correction function 553D, and body movement change monitoring function 552D; and a corresponding flow chart is shown in FIGS. 15, 15A and 15B.

In step (ST1) counter value K (previous measurement value) is fetched from pulse wave period counter 512 for determining reference value $S_{old}$ of the current window, and the various variables to be used for setting the pulse wave period window, etc. are initialized. That is, variable Run used for setting the width of the window for pulse wave period is set to "0", and coefficient Rmax for specifying the upper margin (this corresponds to the lower margin in the window for pulse rate because of the dimensional difference between pulse wave period and pulse rate) of the window for pulse wave period is set to "1.2", and coefficient Rmin for specifying the lower margin (this corresponds to the upper margin in the window for pulse rate because of the dimensional difference between pulse wave period and pulse rate) of the window for pulse wave period is set to "0.8".

Next, in order to initialize the window, the upper margin of the window is set by multiplying reference value $S_{old}$ to which the previous measurement value has been assigned, by Rmax (or 1.2 in the preferred embodiment), and the lower margin of the window is set by multiplying reference value Sold, by Rmin (or 0.8 in the preferred embodiment) (steps ST2 and ST3). That is, the window is set within the range of ±20% of the previous measurement value.

Actual measurement now begins, and pulse wave period S is determined by fetching counter value K of pulse wave period counter 512 (step ST4).

Next, body movement change monitoring function 552D determines the change trend of body movement period. In this process, counter value T of body movement period counter 522 is first fetched into SM as a converted velocity value, and at the same time three adjoining points ($SM_n$, $SM_{n-1}$, and $SM_{n-2}$) stored in RAM 562 are updated to the three points including SM fetched above (step ST5). Next, the differences between $SM_{n-2}$ through $SM_n$ which change over time are determined, and the sum total of these differences, $D_{eff}$ is obtained (step ST6).

Next, variable Run for setting the window is judged whether it is "0" (step ST7). This is performed in order to decide whether or not the upper and lower margins of the window have already been corrected because of large body movements.

If variable Run is "0", whether or not variable Deff for determining the change trend of body movement cycles is determined whether it is equal to or larger than the threshold value SMth (SMth is a positive integer) on the positive side (step ST8). If variable $D_{eff}$ is larger than the threshold value SMth on the positive side, it indicates that the body movement has increased.

In step ST8, even when variable Deff is positive, if its absolute value is equal to or smaller than threshold value SMth, body movements are not present or small enough with little velocity change, and thus the load on the heart does not change much. Therefore, the initially set window is used as is since pulse wave period (pulse rate) should not change much. In other words, window determination function 551 determines whether or not the current pulse wave period S measurement is smaller than lower margin Low (step ST9), and determines whether or not the current pulse wave period S measurement is larger than upper margin High (step ST10). That is, whether or not the current pulse wave period S measurement falls within the window is determined.

If the current pulse wave period S measurement is judged to fall within the window, pulse rate calculation function 554 assigns the current pulse wave period S measurement to pulse rate calculation variable T (step ST11) and then calculates pulse rate M (step ST12). Next, after pulse rate calculation variable T is assigned to reference value $S_{old}$ of the window (step ST13), i.e., after the pulse wave period S measurement is assigned to reference value $S_{old}$, pulse rate M that is obtained is displayed on liquid crystal display device 13 (step ST14), and then the pulse wave measurement results for the next 4 seconds are processed, and pulse wave period S is determined by again fetching counter value K of pulse wave period counter (step ST4).

In contrast, if the current pulse wave period S measurement is judged not to be within the window in steps ST9 or ST10, after reference value $S_{old}$ of the window, i.e., the previous pulse wave period, instead of the current pulse wave period S measurement, is assigned to pulse rate calculation variable T (step ST15), pulse rate M is calculated based on this value (step ST12). Next, after pulse rate calculation variable T is assigned to reference value $S_{old}$ of the window (step ST13), i.e., after the previously measured pulse wave period is assigned to reference value $S_{old}$ as is, pulse rate M that is obtained is displayed on liquid crystal display device 13 (step ST14). Then, the pulse wave measurement results for the next 4 seconds are processed, and pulse wave period S is determined by again fetching counter value K of pulse wave period counter (step ST4).

In step ST8, if variable $D_{eff}$ for determining the change trend of body movements is larger than the positive threshold value SMth, and if at the same time pulse wave period S is judged to be larger than pulse wave period S120 at pulse rate of 120/minute, i.e., pulse rate is confirmed to be equal to or less than 120/minute, window correction function 553D first increments variable Run by "1" (step ST17), and then obtains from the data in Table 1, coefficient Rmax for specifying the upper margin of the window and coefficient Rmin for specifying the lower margin of the window, when variable Run is "1" (step ST18).

Then, a new upper margin High and a new lower margin Low of the window are determined (steps ST19 and ST20).

Next, whether or not the current pulse wave period S measurement falls within the new window is determined (steps ST9 and ST10). Then, the processing in steps ST11 through ST15 are performed as explained in above.

As explained above, because variable Run is "1" and not "0" after the first window correction, step ST21 determines whether or not variable Run is "4". If it is not "4", step ST22 determines whether or not variable Run is "5". If variable Run is not "5", variable Run is incremented by "1" (step ST17), and then coefficient Rmax specifying the upper margin of the window and coefficient Rmin for specifying the lower margin of the window, when variable Run is "2" (step ST18), are obtained from the data in Table 1.

Then, a new upper margin High and a new lower margin Low of the window are determined (steps ST19 and ST20).

Next, whether or not the current pulse wave period S measurement falls within the new window is determined (steps ST9 and ST10). Then, the processing in steps ST11 through ST15 are performed.

This process is performed until variable Run reaches "4", and because each time variable Run is incremented by "1" (step ST17), new coefficients Rmax and Rmin are determined from the table data (step ST18) and window correction is performed (steps ST19 and ST20).

As explained above, window correction circuit 553D makes the upper margin widest immediately after body movement increases, and subsequently returns the upper margin to the pre-correction state as time passes. This is the first correction.

After variable Run reaches "4", the pulse rate should remain high. Therefore, the window is determined based on coefficients Rmax and Rmin when variable Run is "4" (steps ST19 and ST20).

Note however that if variable $D_{eff}$ used for determining the change trend of body movements is equal to or less than the threshold on the negative side, -SMth, in step ST23, it indicates that body movement is decreasing, i.e., the pulse is slowing down and the load on the heart is decreasing, and thus the pulse rate is also decreasing. In this case, step ST24 determines whether or not pulse wave period S is smaller than pulse wave period S150 at pulse rate of 150/minute, i.e., whether or not pulse rate is larger than 150/minute, and if pulse rate is confirmed to be higher than 150/minute, increments variable Run by "1" to "5" (step ST17), and then obtains from the data in Table 1, coefficient Rmax for specifying the upper margin of the window and coefficient Rmin for specifying the lower margin of the window, when variable Run is "5" (step ST18).

Then, a new upper margin High and a new lower margin Low of the window are determined (steps ST19 and ST20).

Next, whether or not the current pulse wave period S measurement falls within the new window is determined (steps ST9 and ST10). Then, the processing in steps ST11 through ST15 are performed.

Content of window correction During the process described above, coefficients Rmax and Rmin are set as shown in the data in Table 2, in this example. Since coefficient Rmax sets the upper margin of the pulse wave period window, it sets the lower margin of the pulse rate window. Conversely, since coefficient Rmin sets the lower margin of the pulse wave period window, it sets the upper margin of the pulse rate window.

TABLE 2

| Variable Run | Specific state | Lower margin Rmin of pulse wave period | Upper margin Rmax of pulse wave period |
|---|---|---|---|
| 0 | Initial setting | ×0.8 | ×1.2 |
| 1 | First 4 seconds after body movements increase | ×0.9 | ×1.8 |
| 2 | Next 4 seconds | ×0.9 | ×1.6 |
| 3 | Next 4 seconds | ×0.9 | ×1.4 |
| 4 | Afterwards | ×0.9 | ×1.2 |
| 5 | After body movements decrease | ×0.4 | ×1.1 |

As shown in Table 2 and FIG. 16A, variable Run begins at "0" and sets the lower margin of pulse wave period 20% longer than the previous measurement value and sets the upper margin of pulse wave period 20% shorter than the previous measurement value. When expressed in terms of pulse rate, the upper margin of pulse rate is set 20% larger than the previous measurement value and the lower margin of pulse rate is set 20% smaller than the previous measurement value.

Then, as shown in FIGS. 16B and 16C, when body movements become larger, variable Run is "1" for the following 4 seconds, and the lower margin of pulse wave period is set 80% wider than the previous measurement value and the upper margin of pulse wave period is set 10% narrower than the previous measurement value. When expressed in terms of pulse rate, the upper margin of pulse rate is set 80% wider than the previous measurement value and the lower margin of pulse rate is set 10% narrower than the previous measurement value.

For the next 4 seconds, variable Run is "2" and the lower margin of pulse wave period is set 60% wider than the previous measurement value and the upper margin of pulse wave period is set 10% narrower than the previous measurement value. When expressed in terms of pulse rate, the upper margin of pulse rate is set 60% wider than the previous measurement value and the lower margin of pulse rate is set 10% narrower than the previous measurement value.

For the next 4 seconds, variable Run is "3" and the lower margin of pulse wave period is set 40% wider than the previous measurement value and the upper margin of pulse wave period is set 10% narrower than the previous measurement value. When expressed in terms of pulse rate, the upper margin of pulse rate is set 40% wider than the previous measurement value and the lower margin of pulse rate is set 10% narrower than the previous measurement value.

After that, variable Run is "4" and the lower margin of pulse wave period is set 20% wider than the previous measurement value and the upper margin of pulse wave period is set 10% narrower than the previous measurement value, and measurements continue with this window width. When expressed in terms of pulse rate, the upper margin of pulse rate is set 20% wider than the previous measurement value and the lower margin of pulse rate is set 10% narrower than the previous measurement value.

The correction performed when variable Run is "1", "2", "3", or "4" is the first correction.

Note that when body movement subsequently decreases, variable Run is "5", and the lower margin of pulse wave period is set 10% wider than the previous measurement value and the upper margin of pulse wave period is set 60% narrower than the previous measurement value. When expressed in terms of pulse rate, the upper margin of pulse rate is set 10% wider than the previous measurement value and the lower margin of pulse rate is set 60% narrower than the previous measurement value.

The correction performed when variable Run is "5" is the second correction.

As explained above, window correction function 553D widens the upper margin of the window, as the first correction, when larger body movements are expected to accelerate the pulse; and widens the lower margin of the window, as the second correction, when smaller body movements are expected to decelerate the pulse, by matching the body movement changes and pulse changes of an actual pattern. Therefore, even when the pulse rate changes greatly, the window can be appropriately determined because it can keep up with the changes. Furthermore, in the first correction, the lower margin of the window is narrowed instead of widening the upper margin, and in the second correction, the lower margin of the window is widened instead of narrowing the upper margin, resulting in higher window determination precision.

Additionally, in the first correction, the upper margin is made widest immediately after body movement increases, and subsequently the upper margin is returned to the pre-correction state as time passes, by matching the actual change pattern. Therefore, the window need not be made unnecessarily wide, resulting in appropriate window determination.

Furthermore, because a slow pulse rate is confirmed before widening the upper margin of the window during the first correction, and a slow pulse rate is confirmed before widening the lower margin of the window during the second correction, the window is always corrected in the right direction.

Another configuration of the body movement change monitoring function

In this embodiment, the fact that the velocity changes as shown in FIGS. 16B and 16C is utilized by body movement change monitoring function 552D for monitoring changes in body movements. However, since the amplitude of the signal that is output from body movement sensor device 90 also changes when body movements change as shown in FIGS. 16B and C, it is possible to correct the window by recognizing body movement changes based on the changes in the amplitude of the signal that is output from body movement sensor device 90.

Fifth Embodiment

In the fourth embodiment, the window for the pulse rate measured by the pulse rate counter was corrected based on velocity trend. Instead, it is also possible to correct the window for velocity measured by the velocity counter, based on the pulse trend. In such a case, the processing detail of the window correction is the same as the flow chart shown in FIG. 15, except that velocity (body movement) and pulse wave period (pulse rate) are swapped and that the upper and lower margins of the window are set to the specified conditions. Therefore, their explanations are omitted. FIG. 17 shows the configurations of the control circuit, etc. that are required for the above-mentioned process.

In FIG. 17, the period and frequency measurement device is first provided with pulse wave detection sensor unit 30 for detecting pulse wave signals, pulse wave signal amplification circuit 511 for amplifying the pulse wave signals output by pulse wave detection sensor unit 30, and pulse wave period counter 512 for counting the time between the edges of the square waves output by the amplification circuit. The period and frequency measurement device is also provided with body movement sensor device 90 for detecting body movement signals, body movement signal amplification circuit 521 for amplifying the body movement signals output by body movement sensor devices, and body movement period counter 522 for counting the time between edges of the square waves output by amplification circuit 521. The period and frequency measurement device is further provided with window determination function 551 that sets a specified reference value based on the previous detection result of body movement sensor device 90 and that determines whether or not the current detection result of body movement sensor device 90 falls within the window defined by the upper and lower margins relative to the reference value, and velocity calculation function 574 that calculates a velocity based on the current detection result of body movement sensor device 90 if this current detection result is within the window.

Processor 55E is provided with pulse change monitoring function 552E (pulse change monitoring means) which monitors whether or not the pulse rate has accelerated, based on the detection result of pulse wave detection sensor unit 30; and with window correction function 553E (window correction means) which performs the first correction, i.e., widening the upper margin of the window for velocity and narrowing the lower margin, if the monitoring result of pulse change monitoring means 552E indicates faster pulses, and subsequently performs the second correction, i.e., widening the lower margin (to which the first correction was applied earlier) and narrowing the upper margin (to which the first correction was applied earlier), if the monitoring result of the pulse change monitoring means 552E indicates slower pulses. In such a configuration, the lower margin of the window is narrowed instead of widening the upper margin in the first correction, and the upper margin of the window is narrowed instead of widening the lower margin in the second correction, by matching the velocity change pattern, enabling appropriate window correction.

Note that window correction function 553E can be configured such that it makes the upper margin widest, in the first correction, immediately after the pulse rate accelerates, and subsequently returns the upper margin to the pre-correction state as time passes. With such a configuration, the upper margin of the window can be corrected by matching the actual velocity change pattern. Therefore, the window need not be made unnecessarily wide, resulting in appropriate window determination.

Furthermore, window correction function 553E can be configured such that it performs the first correction if the monitoring result of pulse change monitoring function 552E indicates that the pulse rate has accelerated and if the previous or the current measured velocity is smaller than a specified value, and performs the second correction if the monitoring result of pulse change monitoring function 552E indicates that the pulse rate has decelerated and if the previous or the current measured velocity is larger than a specified value. With such a configuration, incorrect window correction can be prevented because a slow velocity is confirmed before widening the upper margin of the window, and a fast velocity is confirmed before widening the lower margin of the window.

Another configuration of the pulse wave data processing circuit

For measuring pulse rate, it is possible to first use an operational amplifier to amplify the analog signal that is output by pulse wave detection sensor unit 30, then output the result to an A/D converter via a sample hold circuit, perform frequency analysis (high-speed Fourier transformation: FFT processing) on the pulse wave data that has been converted into a digital signal by the A/D converter, and then to measure pulse rate from the resulting spectrum, instead of measuring the time between edges of the square waves that are output by pulse wave signal amplification circuit 511. Furthermore, for measuring and monitoring velocity, it is possible to first use an operational amplifier to amplify the analog signal that is output by body movement sensor device 90, then output the result to an A/D converter via a sample hold circuit, perform frequency analysis (high-speed Fourier transformation: FFT processing) on the pulse wave data that has been converted into a digital signal by the A/D converter, and then to measure velocity from the resulting spectrum, instead of measuring the time between the edges of the square waves that are output by body movement signal amplification circuit 521.

Although the period measuring means (pulse or body movement) in the above example is configured to obtain the period of the period signal (pulse or body movement), it can also be configured to obtain frequency which is the inverse of period. Since period and frequency correspond univocally to each other, it is possible to select whichever is more convenient in terms of calculation, etc.

It is also possible to treat the one measurement taken immediately before as the current measurement value (pulse rate or velocity), or to treat the average of several measurements taken, including the current one, as the current measurement value (pulse rate or velocity).

Furthermore, in the fourth and fifth embodiments window correction functions 553D and 553E correct the window for the current measurement value because they correct the window before the window for the current measurement value is determined. However, instead of such a configuration, it is possible to perform window correction after the window for the current measurement value is determined. In this case, window correction functions 553D and 553E correct the window for the next measurement value.

As described above, the period and frequency measurement device related to the invention is characterized in that it is provided with a window correction means for reconciling abnormal value elimination by a window determination means with the responsiveness to rapid period fluctuations. Therefore, according to the invention, both reliability and accuracy in measurement during exercise can be achieved at the same time.

In particular, when the amount of correction for the window reference value is optimized by forecasting the rising or falling trend of the pulse rate (or body movement) based on the monitoring result of the body movement change monitoring means (pulse change monitor means), the window can be corrected with appropriate responsiveness to changes even when the pulse rate (body movement) temporarily changes rapidly, such as at the start or end of exercising, or when the velocity fluctuates greatly. Therefore, appropriate window determination can be performed. As a result, the reliability of pulse rate measurement during exercise and running velocity measurement is greatly increased, and pulse rate counters and velocity counters that enables safe and effective training can be provided in the field of sports science.

According to the invention, the upper margin of the window for pulse rate is widened, as the first correction, when increased body movement is expected to accelerate the pulse; the lower margin of the window for pulse rate is widened, as the second correction, when decreased body movement is expected to decelerate the pulse, by matching the body movement changes and pulse changes of an actual pattern, and thus window determination can be appropriately performed because window correction can keep up with the changes even when the pulse rate changes greatly.

Furthermore, when the configuration makes the upper margin widest, in the first correction, immediately after body movement increases, and subsequently returns the upper margin to the pre-correction state as time passes, the window can be corrected by matching the actual change pattern, enabling appropriate window determination.

Additionally, when the lower margin of the window is narrowed, instead of widening the upper margin, as the first correction, and the upper margin of the window is narrowed, instead of widening the lower margin, as the second correction, window determination can be appropriately performed.

Furthermore, when a slow pulse rate is confirmed before widening the upper margin of the window, as the first correction, and a fast pulse rate is confirmed before widening the lower margin of the window, as the second correction, incorrect window correction can be prevented.

When the window for velocity is corrected in the same manner as described above by matching the changes in pulse, for velocity measurement, the same effects can be obtained.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

Reference Numerals

1 Period and frequency measurement device (pulse/velocity counter)
5 Control circuit
10 Device main body
13 Liquid crystal display device (display means)
30 Pulse wave detection sensor unit (pulse wave detection sensor means)
31 LED
32 Phototransistor
55A - E Processors
90 body movement sensor device (body movement detection sensor means)
511 Pulse wave signal amplification circuit
512 Pulse wave period counter
521 Body movement signal amplification circuit
522 Body movement period counter
551 Window determination function (window determination means)
552B, D Body movement change monitoring memory (body movement change monitoring means)
552C, E Pulse change monitoring function (pulse change monitoring means)
553A - E Window correction function (window correction means)
554 Pulse rate calculation function (pulse rate calculation means)
574 Velocity calculation function (velocity calculation means)

What is claimed is:

1. A period and frequency measurement device comprising:

sensor means for measuring pulse waves and body movements;

window determination means for setting a reference value in accordance with previous pulse waves measured by said sensor means or body movements measurement measured by said sensor means, for setting an upper margin and a lower margin relative to the reference value, for defining a window having the upper margin and the lower margin and for determining whether current pulse waves and body movements measurement measured by said sensor means is within the window;

window correction means for correcting at least one of the upper margin and the lower margin to be used for next pulse waves and body movement measurement measured by said sensor means and pulse count calculation means for calculating a pulse rate based on current pulse waves and body movements measurement measured by said sensor means and for applying a specified correction to the current pulse waves and body movements measurement if a determination result of said window determination means indicates that the current pulse waves and body movements measurement by said sensor means is outside a current window.

2. A period and frequency measurement device comprising:

sensor means for measuring pulse waves and body movements;

window determination means for setting a reference value in accordance with previous pulse waves measured by said sensor means and body movements measurement measured by said sensor means, for setting an upper margin and a lower margin relative to the reference value, for defining a window having the upper margin and the lower margin, and for determining whether current pulse waves and body movements measurement measured by said sensor means is within the window:

window correction means for correcting at least one of the upper margin and the lower margin to be used for next pulse waves and body movement measurement measured by said sensor means, and pulse count calculation means for calculating a pulse rate based on current pulse waves and body movements measurement measured by said sensor means and for applying a specified correction to the current ipulse waves and body movements measurement if a determination result of said window determination means indicates that the current pulse waves and body movements measurement by said sensor means is outside a current window, wherein said window correction means further for incrementing the current pulse waves and body movements measurement and for setting a new reference value if a determination result of said window determination means indicates that the current pulse wave and body measurement exceeds the upper margin of the window and wherein said window correction means for decrementing the current pulse waves and body movement measurement for setting a new reference value if the determination result of the window determination means indicates that the current pulse waves and body movement measurement is below the lower margin of the window.

3. A period and frequency measurement device comprising:

sensor means for measuring pulse waves and body movements:

window determination means for setting a reference value in accordance with previous pulse waves measured by said sensor means and body movements measurement measured by said sensor means, for setting an upper margin and a lower margin relative to the reference value.

for defining a window having the upper margin and the lower margin and for determining whether current pulse waves and body movements measurement measured by said sensor means is within the window;

window correction means for correcting at least one of the upper margin and the lower margin to be used for next pulse waves and body movement measurement measured by said sensor means, and pulse count calculation means for calculating a pulse rate based on current pulse waves and body movements measurement measured by said sensor means and for applying a specified correction to the current pulse waves and body movements measurement if a determination result of said window determination means indicates that the current pulse waves and body movements measurement by said sensor means is outside a current window, wherein said calculation means further for calculating status values comprising pulse rate and velocity based on the current pulse waves and body movements measurement if the determination result of said window determination means indicates that the current pulse waves and body movements measurement measured by said sensor means is within the window, and for calculating status values comprising pulse rate and velocity based on the reference values generated by said window correction means if the determination result of the window determination means indicates that the current pulse and body measurements measurement values measured by said sensor means is outside the window; and wherein said period and frequency measurement device further comprises display means for displaying the status values calculated by said calculation means.

4. A period and frequency measurement device comprising:

sensor means for measuring pulse waves and body movements;

window determination means for setting a reference value in accordance with previous pulse waves measured by said sensor means and body movements measurement measured by said sensor means, for setting an upper margin and a lower margin relative to the reference value, for defining a window having the upper margin and the lower margin, and for determining whether current pulse waves and body movements measurement measured by said sensor means is within the window;

window correction means for correcting at least one of the upper margin and the lower margin to be used for next pulse waves and body movement measurement measured by said sensor means; and pulse count calculation means for calculating a pulse rate based on current pulse waves and body movements measurement measured by said sensor means and for applying a specified correction to the current pulse waves and body movements measurement if a determination result of said window determination means indicates that the current pulse waves and body movements measurement by said sensor means is outside a current window, wherein said window determination means for setting the upper margin equal to the lower margin.

5. A period and frequency measurement device comprising:

body movement detection sensor means for measuring body movements;

pulse wave detection sensor means for measuring pulse wave, wherein a measurement value is defined as at least one of the body movements measured by said body movement sensor means and the pulse waves measured by said pulse wave sensor means;

window determination means for setting a reference value based on the measurement value, for setting an upper margin and a lower margin relative to the reference value, for defining a window having the upper margin and the lower margin, and for determining whether a current measurement value is within the window;

change monitoring means for monitoring a change in the measurement value by one of said body movement detection sensor means and said pulse wave detection sensor means defining a first sensor means; and window correction means for correcting the window to be used for one of the current measurement value and a next measurement value by the other one of said body movement detection sensor means and said pulse waves detection sensor means, defining a second sensor means, based on a monitoring result of said change monitoring means.

6. The period and frequency measurement device according to claim 5, wherein said change monitoring body movement change monitoring means for monitoring body movement changes based on the measurement values of said body movement detection sensor means.

7. A period and frequency measurement device comprising:

body movement detection sensor means for measuring body movements;

pulse wave detection sensor means for measuring pulse wave, wherein a measurement value is defined as at least one of the body movements measured by said body movement sensor means and the pulse waves measured by said pulse wave sensor means;

window determination means for setting a reference value based on the measurement value, for setting an upper margin and a lower margin relative to the reference value, for defining a window having the upper margin and the lower margin, and for determining whether a current measurement value is within the window, change monitoring means for monitoring a change in the measurement value by one of said body movement detection sensor means and said pulse wave detection sensor means defining a first sensor means; and window correction means for correcting the window to be used for one of the current measurement value and a next measurement value by the other one of said body movement detection sensor means and said pulse waves detection sensor means, defining a second sensor means, based on a monitoring result of said change monitoring means, wherein said window correction means for correcting the window for a next measurement value measured by said pulse wave detection sensor means, by incrementing the current measurement value measured by said pulse wave detection sensor means and using the result as a new reference value if the determination result of said window determination means indicates that the current measurement value measured by said pulse wave detection sensor means is outside the window and if the monitoring result by said body movement change monitoring means indicates that body movement has increased; and by decrementing the current measurement value measured by said pulse wave detection sensor means and using the result as a new reference value if the determination result of said window determination means indicates that the current measurement measured by said pulse wave detection sensor means is outside the window and if the monitoring result by said body movement change monitoring means indicates that body movement has decreased.

8. The period and frequency measurement device according to claim 7, further comprising a pulse rate calculation means for calculating pulse rate based on the current measurement value if the determination result of said window determination means indicates that the current measurement measured by said pulse wave detection sensor means is within the window, and for calculating pulse rate based on the reference value generated from the measurement values by said window correction means if the determination result of the window determination means indicates that the current measurement value measured by said pulse wave detection sensor means is outside the window; and a display means for displaying the pulse rate calculated by said pulse rate calculation means.

9. The period and frequency measurement device according to claim 7, wherein said window correction means for further performing corrections in proportion to a difference between an amount of body movement, determined based on the monitoring result of said body movement change monitoring means, and the current measurement measured by said pulse wave detection sensor means.

10. The period and frequency measurement device according to claim 7 wherein said window determination means for setting the upper margin equal to the lower margin.

11. A period and frequency measurement device comprising:

body movement detection sensor means for measuring body movements;

pulse wave detection sensor means for measuring pulse wave, wherein a measurement value is defined as at least one of the body movements measured by said body movement sensor means and the pulse waves measured by said pulse wave sensor means:

window determination means for setting a reference value based on the measurement value, for setting an upper margin and a lower margin relative to the reference value, for defining a window having the upper margin and the lower margin and for determining whether a current measurement value is within the window;

change monitoring means for monitoring a change in the measurement value by one of said body movement detection sensor means and said pulse wave detection sensor means defining a first sensor means; and window correction means for correcting the window to be used for one of the current measurement value and a next measurement value by the other one of said body movement detection sensor means and said pulse waves detection sensor means, defining a second sensor means, based on a monitoring result of said change monitoring means, wherein said change monitoring body movement change monitoring means for monitoring body movement changes based on the measurement values of said body movement detection sensor means, wherein said window correction means further for correcting the window to be used for one of the current measurement value and the next measurement value measured by said pulse wave detection sensor means, for performing a first correction by widening the upper margin, if the monitoring result of said body movement change monitoring means indicates increased body movement, and for performing a second correction by widening the lower margin, if the monitoring result of said body movement change monitoring means indicates decreased body movement.

12. The period and frequency measurement device according to claim 11, wherein said window correction means for further setting the upper margin widest in the first correction, immediately after body movement increases, and subsequently for further setting the upper margin to a pre-correction state during subsequent measurements.

13. The period and frequency measurement device according to claim 11, wherein said window correction means further for narrowing the lower margin, in the first correction, immediately after body movement increases, and further for narrowing the upper margin, in the second correction, immediately after body movement decreases.

14. The period and frequency measurement device according claim 11, wherein said window correction means further for performing the first correction when the monitoring result of said body movement change monitoring means indicates increased body movement and one of the previous and the current measurement value measured by said pulse wave detection sensor means is less than a first specified value, and further for performing the second correction when the monitoring result of said body movement change monitoring means indicates decreased body movement and one of the previous and the current measurement values measured by said pulse wave detection sensor means is greater than a second specified value.

15. A user wearable device comprising:

a main body having a period and frequency measurement device comprising:

sensor means for measuring pulse waves and body movements;

window determination means for setting a reference value in accordance with previous pulse waves measured by said sensor means and body movements measurement measured by said sensor means for setting an upper margin and a lower margin relative to the reference value for defining a window having the upper margin and the lower margin, and for determining whether current pulse waves and body movements measurement measured by said sensor means is within the window; and window correction means for correcting at least one of the upper margin and the lower margin to be used for next pulse waves and body movement measurement measured by said sensor means, by applying a specified correction to the current pulse waves and body movements measurement if a determination result of said window determination means indicates that the current pulse waves and body movements measurement by said sensor means is outside a current window, and a band secured to said main body for removably fastening said main body to a user.

16. The user wearable device according to claim 15, wherein said window determination means for setting the upper margin equal to the lower margin.

17. The user wearable device according to claim 15 wherein said main body further comprises a watch.

18. A user wearable device comprising:

a main body having a -period and frequency measurement device comprising:

sensor means for measuring pulse waves and body movements, window determination means for setting a reference value in accordance with previous pulse waves measured by said sensor means and body movements measurement measured by said sensor means for setting an upper margin and a lower margin relative to the reference value, for defining a window having the upper margin and the lower margin, and for determining whether current pulse waves and body movements measurement measured by said sensor means is within the window: and window correction means for correcting at least one of the upper margin and the lower margin to be used for next pulse waves and body movement measurement measured by said sensor means, by applying a specified correction to the current pulse waves and body movements measurement if a determination result of said window determination means indicates that the current pulse waves and body movements measurement by said sensor means is outside a current window, and a band secured to said main body for removably fastening said main body to a user, wherein said window correction means further for incrementing the current pulse waves and body movements measurement and sets a new reference value if a determination result of said window determination means indicates that the current pulse wave and body measurement exceeds the upper margin of the window and wherein said window correction means further for decrementing the current pulse waves and body movement measurement for setting a new reference value if the determination result of the window determination means indicates that the current pulse waves and body movement measurement is below the lower margin of the window.

19. A method for measuring period and frequency comprising the steps of:

measuring pulse waves and body movements;

setting a reference value in accordance with previously measured pulse waves and body movements;

setting an upper margin and a lower margin relative to the reference value;

defining a window having the upper margin and the lower margin;

determining whether currently measured pulse waves and body movements measurement are within the window; and correcting at least one of the upper margin and the lower margin to be used for next pulse waves and body movement measurement, by applying a specified correction to the current pulse waves and body movements measurement if a determination result of said window determination step indicates that the current pulse waves and body movements measurement is outside a current window.

20. A method for measuring period and frequency comprising the steps of: measuring body movements;

measuring pulse wave, wherein a measurement value is defined as at least one of the measured body movements and the measured pulse waves;

setting a reference value based on the measurement value, for setting an upper margin and a lower margin relative to the reference value;

for defining a window having the upper margin and the lower margin, determining whether a current measurement value is within the window;

monitoring a change in the measurement value in one of said body movement measurement step and said pulse wave measurement step; and correcting the window to be used for one of the current measurement value and a next measurement value by the other one of said body movement measurement step and said pulse wave measurement step, based on a monitoring result of said change monitoring step.

* * * * *

UNITED STATES PATENT AND TRADEMARK OFFICE
CERTIFICATE OF CORRECTION

PATENT NO. : 5,759,156
DATED : June 2, 1998
INVENTOR(S) : Motomu Hayakawa, et. al.

It is certified that error appears in the above-identified patent and that said Letters Patent is hereby corrected as shown below:

Title page, item [73] Assignee: change "Seiko Epson Corporation; Seiko Instruments, Inc., both of Tokyo, Japan" to --Seiko Epson Corporation, Tokyo; Seiko Instruments, Inc., Chiba-ken, both of Japan--.

Column 26, line 14, insert --,-- after "lower margin".
    line 50, change "means," to --means;--.
    line 54 change "ipulse" to --pulse--.

Column 27, line 19, insert --,-- after "lower margin".
    line 26, change "means," to --means;--.

Column 30, line 6, insert --,-- after "lower margin".

Column 31, line 4, insert --,-- after "reference value".
    line 18, change "window," to --window;--.
    line 27, change "-period" to --period--.
    line 42, change "window:" to --window;--.
    line 52, change "window," to --window;--.

UNITED STATES PATENT AND TRADEMARK OFFICE
CERTIFICATE OF CORRECTION

PATENT NO. : 5,759,156
DATED : June 2, 1998
INVENTOR(S) : Motomu Hayakawa, et. al.

It is certified that error appears in the above-identified patent and that said Letters Patent is hereby corrected as shown below:

Column 32, line 23, change "currently" to --currently--.

line 39, change "value," to --value;--.

line 43, change "lower margin," to --lower margin;--.

Signed and Sealed this

Twentieth Day of October, 1998

*Attest:*

BRUCE LEHMAN

*Attesting Officer*     *Commissioner of Patents and Trademarks*